(12) United States Patent
Kakiuchi et al.

(10) Patent No.: US 9,180,201 B2
(45) Date of Patent: Nov. 10, 2015

(54) METHOD FOR PREPARING LIPOPEPTIDE COMPOUND

(75) Inventors: Nobuyuki Kakiuchi, Funabashi (JP); Takeaki Shoji, Funabashi (JP); Kazuki Hirasada, Funabashi (JP); Keigo Matsumoto, Funabashi (JP); Hiroki Yamaguchi, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 13/394,243

(22) PCT Filed: Sep. 7, 2010

(86) PCT No.: PCT/JP2010/065334
§ 371 (c)(1),
(2), (4) Date: May 18, 2012

(87) PCT Pub. No.: WO2011/027897
PCT Pub. Date: Mar. 10, 2011

(65) Prior Publication Data
US 2012/0253012 A1  Oct. 4, 2012

(30) Foreign Application Priority Data
Sep. 7, 2009  (JP) .................. 2009-205855

(51) Int. Cl.
| | | |
|---|---|---|
| *C07K 1/02* | (2006.01) | |
| *C07K 1/107* | (2006.01) | |
| *C07K 5/06* | (2006.01) | |
| *A61K 47/48* | (2006.01) | |
| *A61K 38/05* | (2006.01) | |
| *C07K 5/062* | (2006.01) | |

(52) U.S. Cl.
CPC ............ *A61K 47/48046* (2013.01); *A61K 38/05* (2013.01); *C07K 1/026* (2013.01); *C07K 1/107* (2013.01); *C07K 1/1072* (2013.01); *C07K 1/1075* (2013.01); *C07K 5/06* (2013.01); *C07K 5/06026* (2013.01); *C07K 5/06043* (2013.01); *C07K 5/06052* (2013.01)

(58) Field of Classification Search
USPC ........................................................ 530/333
See application file for complete search history.

(56) References Cited

U.S. PATENT DOCUMENTS

2005/0027120 A1 *  2/2005  Gojon-Zorrilla ............. 544/105
2008/0200704 A1 *  8/2008  Chaudhuri et al. ............. 554/35

FOREIGN PATENT DOCUMENTS

| JP | 9255675 | * | 9/1997 | ............. A01N 43/08 |
| WO | WO 2009/005151 A1 | | 1/2009 | |
| WO | WO 2009/005152 A1 | | 1/2009 | |
| WO | WO 2009/005151 | * | 8/2009 | ............. C07K 5/103 |
| WO | WO 2010/013555 A1 | | 2/2010 | |

OTHER PUBLICATIONS

Chikao et al., Nippon Kagakkai Koen Yokoshu (2004) 84(2), 1011.*
Hashimoto et al., Nippon Kagakkai Koen Yokoshu (2004) 84(2), 1011.*
Yang et al., "Conjugates of Naphthalene and Dipeptides Produce Molecular Hydrogelators with High Efficiency of Hydrogelation and SuperHelical Nanofibers," *Journal of Materials Chemistry*, 2007, pp. 850-854, vol. 17, The Royal Society of Chemistry.
Li et al., "Synthesis of L-Carnosine," *Journal of South China Normal University*, 2007, No. 2, pp. 89-92, China.

(Continued)

*Primary Examiner* — Marcela M Cordero Garcia
*Assistant Examiner* — Catherine Mader
(74) *Attorney, Agent, or Firm* — Oliff PLC

(57) ABSTRACT

There is provided a practical method for preparing lipopeptide compounds, which method is capable of inexpensive mass production without requiring complicated operations. The lipopeptide compound of formula (3):

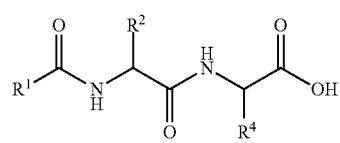

is produced by reacting an ester compound of formula (1):

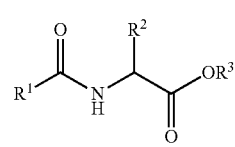

with an α-amino acid compound of formula (2):

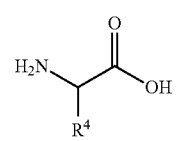

in the presence of a base and within a solvent containing a nonpolar organic solvent.

18 Claims, 5 Drawing Sheets

(56) References Cited

OTHER PUBLICATIONS

Yokozeki et al., "A Novel and Efficient Enzymatic Method for the Production of Peptides from Unprotected Starting Materials," *Journal of Biotechnology*, 2005, pp. 211-220, vol. 115, Elsevier B.V.

Dec. 14, 2010 International Search Report issued in International Patent Application No. PCT/JP2010/065334 (with translation).

\* cited by examiner

METHOD FOR PREPARING LIPOPEPTIDE COMPOUND

TECHNICAL FIELD

The present invention relates to a novel method of preparing lipopeptide compounds.

BACKGROUND ART

Functional gels that have been conferred with various capabilities, such as a substance retaining ability, an ability to respond to external stimuli and, out of concern for the environment, biodegradability, have recently being attracting attention.

For example, peptide derivatives composed of a combination of a biocomponent such as a peptide chain (hydrophilic moiety) and an alkyl chain (hydrophobic moiety) are expected to see use as starting materials and intermediates in pharmaceutical products and agricultural chemicals, and also, as materials having amphiphilic properties, in gelators, thickeners and the like. For instance, it has been reported that the dipeptide compounds which have a special lipid moiety and are referred to as "2-(naphthalen-2-yloxy)acetic acid"+ "glycylglycine or glycylserine, etc." become hydrogels (Non-Patent Document 1):

Recently, novel lipopeptides composed of glycine or histidine bonded to palmitic acid or the like have been disclosed as such lipopeptide compounds (see, for example, Patent Documents 1 and 2). Methods for the preparation of such lipopeptides that involve solid phase peptide synthesis have been disclosed, although such methods are capable only of synthesizing a small amount of product and are thus poorly suited for mass production.

There has also been reported, as a method involving the liquid phase synthesis of a lipopeptide compound, a reaction for obtaining N-(1-cyanoaceto)-histidine by reacting ethyl 1-cyanoacetate with histidine in the presence of sodium ethoxide (Non-Patent Document 2).

In addition, a method for amidating histidine and an ester compound that involves the use of an enzyme in water has been reported (Non-Patent Document 3).

In the above examples from the literature, with regard not only to histidine (His)-terminated lipopeptide compounds, but also lipopeptide compounds terminating with arginine (Arg), asparagine (Asn), glutamine (Gln), lysine (Lys) or tryptophan (Trp), no cases have been described in which the reaction is carried out in a mixed solvent composed of a non-polar organic solvent and an alcohol solvent.

Patent Document 1: WO 2009/005151
Patent Document 2: WO 2009/005152
Non-Patent Document 1: Z. Yang, B. Xu et al., *J. Mater. Chem.* 2007, 17, 850-854.
Non-Patent Document 2: *Huanan Shifan Daxue Xuebao, Ziran Kexueban* (2007), (2), 89-92.
Non-Patent Document 3: Yokozeki, Kenzo; Hara, Seiichi; *Journal of Biotechnology* (2005), 115 (2), 211-220.

SUMMARY OF THE INVENTION

Problem to be Solved by the Invention

The object of the present invention is to provide a practical method for preparing lipopeptide compounds, which method is capable of inexpensive mass production without requiring complicated operations.

Means for Solving the Problem

The inventors have conducted extensive investigations in order to achieve the above object. As a result, they have discovered that, when the amino group on an amino acid and an ester compound are amidated, by carrying out the reaction in the presence of a base and within a solvent containing a nonpolar organic solvent, a lipopeptide compound can be directly obtained without the use of protecting groups.

Accordingly, the invention relates to:

1. A method of preparing a lipopeptide compound of formula (3):

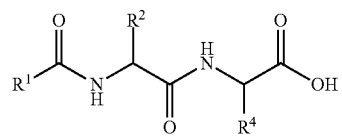

(where $R^1$ is a $C_{9-23}$ aliphatic group; $R^2$ is a hydrogen atom or a $C_{1-4}$ alkyl group which may have a $C_{1-2}$ branch; and $R^4$ is a $-(CH_2)_n-X$ group in which n is a number from 1 to 4 and X is an amino group, a guanidino group, a $-CONH_2$ group, a 5-membered or 6-membered ring which may contain from 1 to 3 nitrogen atoms, or a fused heterocycle composed of a 5-membered ring and a 6-membered ring) or a pharmaceutically usable salt thereof, the method characterized by including: reacting an ester compound of formula (1):

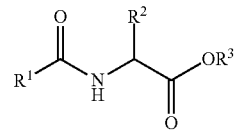

(where $R^1$ and $R^2$ are as defined above, and $R^3$ is a $C_{1-6}$ alkyl group, a $C_{1-6}$ haloalkyl group, a $C_{1-6}$ hydroxyalkyl group, or an aryl group which may be substituted with a $C_{1-6}$ alkyl group) with an α-amino acid compound of formula (2):

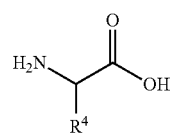

(where $R^4$ is as defined above) in the presence of a base and within a solvent containing a nonpolar organic solvent.

2. The preparation method according to item 1, characterized in that the solvent contains a nonpolar organic solvent and an alcohol.

3. The preparation method according to item 1, wherein either n is a number from 1 to 4 and X is an amino group, a guanidino group or a $-CONH_2$ group, or n is 1 and X is a pyrrole group, an imidazole group, a pyrazole group or an imidazole group.

4. The preparation method according to item 1, wherein $R^1$ is a $C_{11-21}$ linear aliphatic group which may have from 0 to 2 unsaturated bonds.

5. The preparation method according to item 1, wherein $R^2$ is a hydrogen atom or a $C_{1-3}$ alkyl group which may have a $C_1$ branch.
6. The preparation method according to item 1, wherein $R^2$ is a hydrogen atom, methyl, ethyl, n-propyl, isopropyl, n-butyl, isobutyl, sec-butyl or tert-butyl group; and $R^4$ is an aminomethyl, aminoethyl, 3-aminopropyl, 4-aminobutyl, carbamoylmethyl, 2-carbamoylethyl, 3-carbamoylbutyl, 2-guanidinoethyl, 3-guanidinopropyl, pyrrolemethyl, imidazolemethyl, pyrazolemethyl or 3-indolemethyl group.
7. The preparation method according to item 6, wherein $R^2$ is a hydrogen atom, methyl, isopropyl, isobutyl or sec-butyl group; and $R^4$ is a 4-aminobutyl, carbamoylmethyl, 2-carbamoylethyl, 3-guanidinopropyl, imidazolemethyl or 3-indolemethyl group.
8. The preparation method according to item 1, wherein $R^3$ is a methyl or ethyl group.
9. The preparation method according to any one of item 1 to 8, wherein the base is at least one selected from among alkali metals, inorganic acid salts of alkali metals, alkali metal hydroxides, alkali metal alkoxides, alicyclic amines, and alcohol solutions or alcohol dispersions thereof.
10. The preparation method according to item 9, wherein the base is at least one selected from among metallic sodium, metallic potassium, sodium carbonate, potassium carbonate, potassium phosphate, sodium phosphate, sodium hydroxide, potassium hydroxide, sodium methoxide, sodium ethoxide, potassium methoxide, potassium ethoxide, potassium t-butoxide, 1,8-diazabicyclo[5.4.0]-7-undecene, 1,5-diazabicyclo[4.3.0]-5-nonene, and alcohol solutions or alcohol dispersions thereof.
11. The preparation method according to item 10, wherein the base is selected from among sodium methoxide and methanol solutions or methanol dispersions thereof.
12. The preparation method according to any one of items 1 to 11, wherein the nonpolar organic solvent is at least one selected from the group consisting of aromatic compounds, saturated aliphatic compounds and unsaturated aliphatic compounds.
13. The preparation method according to item 12, wherein the nonpolar organic solvent is at least one selected from the group consisting of toluene, xylene, o ortho-dichlorobenzene, pentane, hexane, heptane, octane, cyclopentane, cyclohexane, methylcyclohexane, cycloheptane and 1-hexene.
14. The preparation method according to item 2, wherein the solvent includes cyclohexane and methanol or ethanol.
15. The preparation method according to any one of items 1 to 14, wherein the reaction of the ester compound of formula (1) with the α-amino acid compound of formula (2) is carried out at a reaction temperature of 60±5° C.
16. The preparation method according to any one of items 1 to 15, which includes a step of neutralizing with a hydrogen halide a product obtained from the reaction of the ester compound of formula (1) with the α-amino acid compound of formula (2).
17. The preparation method according to item 16, wherein the neutralization step is carried out in a solvent containing water and an alcohol.
18. A method of preparing a lipopeptide compound of formula (3):

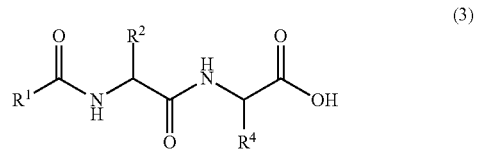

(where $R^1$ is a $C_{9-23}$ aliphatic group; $R^2$ is a hydrogen atom or a $C_{1-4}$ alkyl group which may have a $C_{1-2}$ branch; and $R^4$ is a hydrogen atom, a $C_{1-7}$ alkyl group which may have a $C_{1-3}$ branch, a phenylmethyl group, a phenyethyl group, a $-(CH_2)_n-X$ group in which n is a number from 1 to 4 and X is an amino group, a guanidino group, a $-CONH_2$ group, a 5-membered or 6-membered ring which may contain from 1 to 3 nitrogen atoms, or a fused heterocycle composed of a 5-membered ring and a 6-membered ring) or a pharmaceutically usable salt thereof,
the method characterized by including:
a step of reacting a compound of formula (4)

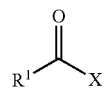

(where X is a halogen atom, a $C_{1-6}$ alkoxy group, or a $-OC(O)R^1$ group in which $R^1$ is as defined above) with a compound of formula (5):

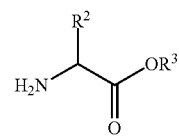

(where $R^2$ is as defined above, and $R^3$ is a $C_{1-6}$ alkyl group, a $C_{1-6}$ haloalkyl group, a $C_{1-6}$ hydroxyalkyl group, or an aryl group which may be substituted with a $C_{1-6}$ alkyl group) to obtain an ester compound of formula (1):

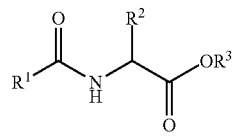

(where $R^1$, $R^2$ and $R^3$ are as defined above); and
a step of reacting the ester compound of formula (1) with an α-amino acid compound of formula (2):

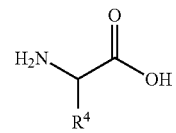

(where $R^4$ is as defined above) in the presence of a base and within a solvent containing a nonpolar organic solvent.

Effects of the Invention

The preparation method of the present invention enables a desired lipopeptide compound to be obtained in a high yield.

Moreover, because the preparation method of the present invention is not accompanied by racemization of the amino acid used, requires no complicated protecting and deprotecting operations, and does not use the expensive reagent known as a condensing agent, it is a practical method of preparation which can be utilized as an industrial production process.

In addition, because the target lipopeptide compound has the ability to gel, it can be employed even in cases where isolating the free form of the compound is difficult.

MODES FOR CARRYING OUT THE INVENTION

Figure 1:
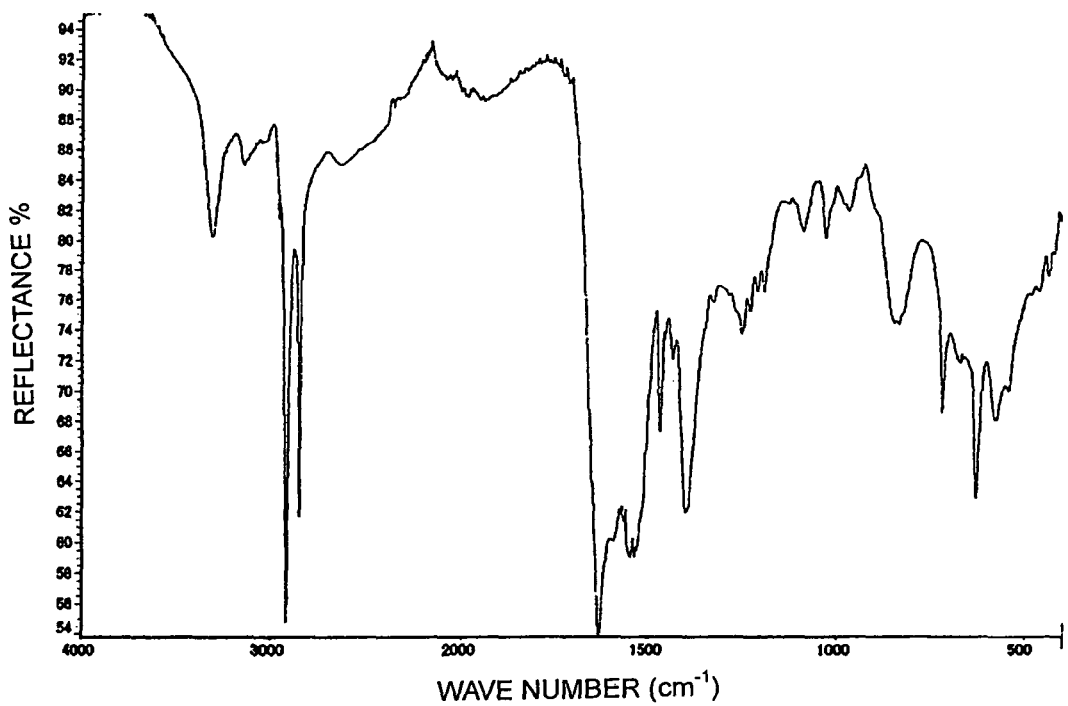
FIG. 1 shows the IR spectrum of the N-palmitoyl-Gly-His obtained in Example 20.

As noted above, various methods have been proposed for preparing lipopeptide compounds, although there has existed a need for a method which is capable of large-volume production without requiring complicated operations such as the protection and deprotection of functional groups and expensive condensing agents or protective group reagents.

For example, in the method described in Non-Patent Document 2, following the reaction, it is difficult to remove the high-boiling, highly polar dimethylformamide (DMF) used as the solvent. When attempts have been made to prepare the lipodipeptide compounds that are the object of the present invention by the methods described in Non-Patent Document 2 and Non-Patent Document 3, problems such as gelling of the DMF or water serving as the reaction solvent have occurred.

The inventors have discovered that, in the preparation of an ester compound of formula (1), by utilizing $R^3$ as a protecting group, improvements in the yield of the product and ease of operation are achieved, in addition to which the —$OR^3$ moiety that has formed as a result can be utilized as a leaving group in subsequent amidation with the α-amino acid compound of formula (2), thus resulting in a method of preparation which has an excellent cost-effectiveness, generates little waste and has a low environmental impact.

In addition, a nonpolar solvent and an alcohol that is immiscible therewith at room temperature are used as the reaction solvents, the reaction being effected under heated conditions in a state where these reaction solvents have become a substantially uniform mixed solvent. Following reaction completion, the reaction mixture is cooled, causing it to separate into a nonpolar solvent and an alcohol solution containing as the product a salt (e.g., an alkali metal salt) of the lipopeptide compound, thus enabling easy recovery and discarding of the nonpolar solvent.

Moreover, by using a nonpolar solvent, unlike in the case of DMF or water which have thitherto been used in the preparation of lipopeptide compounds, following reaction completion and cooling, gelling can be prevented.

The use of an aqueous solution of a hydrogen halide in an amount necessary to neutralize the humoral (alkalinity) of the alcohol solution following reaction made it possible to complete neutralization without associated gelling, enabling easy recovery of the lipopeptide compound in its free form.

It was thus discovered that a lipopeptide compound can be easily synthesized in a high yield without accompanying racemization of the amino acid used, which discovery ultimately led to the present invention.

The present invention is described more fully below.

In this specification, "n" stands for normal, "i" for iso, "s" or "sec" for secondary, "t" or "tert" for tertiary, "c" for cyclo, "o" for ortho, "m" for meta and "p" for para. "Me" refers to a methyl group, "Bu" to a butyl group, and "tBu" to a tertiary butyl group.

In formula (1), $R^1$ is a $C_{9-23}$ aliphatic group. It is desirable for $R^1$ to be preferably a $C_{11-21}$ linear aliphatic group or a $C_{11-21}$ linear aliphatic group having one or two unsaturated bonds.

Here, especially preferred examples of aliphatic groups represented by $R^1$ include nonyl, decyl, undecyl, dodecyl (lauryl), tridecyl, tetradecyl (myristyl), pentadecyl, hexadecyl (palmityl), heptadecyl (margaryl), octadecyl (stearyl), nonadecyl, icosyl and henicosyl groups.

In formula (1), $R^2$ is a hydrogen atom or a $C_{1-4}$ alkyl group which may have a $C_{1-2}$ branch.

In $R^2$ above, a "$C_{1-4}$ alkyl group which may have a $C_{1-2}$ branch" refers to an alkyl group having a main chain of 1 to 4 carbons and a branch of 1 or 2 carbon atoms. Illustrative examples include methyl, ethyl, n-propyl, i-propyl, n-butyl, i-butyl, sec-butyl and tert-butyl groups.

$R^2$ is preferably a hydrogen atom or a $C_{1-3}$ alkyl which may have a $C_1$ branch, and is more preferably a hydrogen atom. Here, "a $C_{1-3}$ alkyl which may have a $C_1$ branch" refers to an alkyl group having a main chain of 1 to 3 carbon atoms and a branch of 1 carbon atom. Illustrative examples include methyl, ethyl, n-propyl, i-propyl, i-butyl and sec-butyl groups. Methyl, i-propyl, i-butyl and sec-butyl groups are preferred.

In above formula (1), $R^3$ is a $C_{1-6}$ alkyl group, a $C_{1-6}$ haloalkyl group, a $C_{1-6}$ hydroxyalkyl group, or an aryl group which may be substituted with a $C_{1-6}$ alkyl group.

Here, preferred examples of alkyl groups represented by $R^3$ include methyl, ethyl, n-propyl, i-propyl, n-butyl, i-butyl, sec-butyl and tert-butyl groups; methyl and ethyl groups are more preferred.

In above formula (2), $R^4$ is a hydrogen atom, a $C_{1-7}$ alkyl group which may have a $C_{1-3}$ branch, a phenylmethyl group, phenylethyl group or a —$(CH_2)_n$—X group, and is preferably a —$(CH_2)_n$—X group.

In the —$(CH_2)_n$—X group, n is a number from 1 to 4 and X is an amino group, a guanidino group, a —$CONH_2$ group, a 5-membered or 6-membered ring which may contain from 1 to 3 nitrogen atoms, or a fused heterocycle composed of a 5-membered ring and a 6-membered ring.

In the above —(CH$_2$)$_n$—X group, X is preferably an amino group, a guanidino group, a —CONH$_2$ group, a pyrrole group, an imidazole group, a pyrazole group or an indole group, and is more preferably an imidazole group. In the above —(CH$_2$)$_n$— group, n is preferably 1 or 2, and more preferably 1.

Hence, the above —(CH$_2$)$_n$— group is preferably an aminomethyl, 2-aminoethyl, 3-aminopropyl, 4-aminobutyl, carbamoylmethyl, 2-carbamoylethyl, 3-carbamoylbutyl, 2-guanidinoethyl, 3-guanidinopropyl, pyrrolemethyl, imidazolemethyl, pyrazolemethyl or 3-indolemethyl; more preferably 4-aminobutyl, carbamoylmethyl, 2-carbamoylethyl, 3-guanidinopropyl, imidazolemethyl or 3-indolemethyl group; and even more preferably an imidazolemethyl group.

Therefore, preferred examples of the lipopeptide compound of above formula (3) include the following compounds formed from a lipid moiety and a dipeptide moiety, where the amino acid abbreviations used are histidine (His), glycine (Gly), valine (Val), isoleucine (Ile), alanine (Ala), arginine (Arg), asparagine (Asn), glutamine (Gln), leucine (Leu), lysine (Lys) and tryptophan (Trp): N-lauroyl-Gly-His, N-lauroyl-Gly-Trp, N-lauroyl-Gly-Gln, N-lauroyl-Gly-Asn, N-lauroyl-Gly-Arg, N-lauroyl-Gly-Lys, N-lauroyl-Ala-His, N-lauroyl-Ala-Trp, N-lauroyl-Ala-Gln, N-lauroyl-Ala-Asn, N-lauroyl-Ala-Arg, N-lauroyl-Ala-Lys, N-lauroyl-Val-His, N-lauroyl-Val-Trp, N-lauroyl-Val-Gln, N-lauroyl-Val-Asn, N-lauroyl-Val-Arg, N-lauroyl-Val-Lys, N-lauroyl-Leu-His, N-lauroyl-Leu-Trp, N-lauroyl-Leu-Gln, N-lauroyl-Leu-Asn, N-lauroyl-Leu-Arg, N-lauroyl-Leu-Lys, N-lauroyl-Ile-Asn, N-myristoyl-Gly-His, N-myristoyl-Gly-Trp, N-myristoyl-Gly-Gln, N-myristoyl-Gly-Asn, N-myristoyl-Gly-Arg, N-myristoyl-Gly-Lys, N-myristoyl-Ala-His, N-myristoyl-Ala-Trp, N-myristoyl-Ala-Gln, N-myristoyl-Ala-Asn, N-myristoyl-Ala-Arg, N-myristoyl-Ala-Lys, N-myristoyl-Val-His, N-myristoyl-Val-Trp, N-myristoyl-Val-Gln, N-myristoyl-Val-Asn, N-myristoyl-Val-Arg, N-myristoyl-Val-Lys, N-myristoyl-Leu-His, N-myristoyl-Leu-Trp, N-myristoyl-Leu-Gln, N-myristoyl-Leu-Asn, N-myristoyl-Leu-Arg, N-myristoyl-Leu-Lys, N-myristoyl-Ile-His, N-myristoyl-Ile-Trp, N-myristoyl-Ile-Asn, N-myristoyl-Ile-Arg, N-myristoyl-Ile-Lys, N-palmitoyl-Gly-Trp, N-palmitoyl-Gly-Gln, N-palmitoyl-Gly-Asn, N-palmitoyl-Gly-Arg, N-palmitoyl-Gly-Lys, N-palmitoyl-Ala-His, N-palmitoyl-Ala-Trp, N-palmitoyl-Ala-Gln, N-palmitoyl-Ala-Asn, N-palmitoyl-Ala-Arg, N-palmitoyl-Ala-Lys, N-palmitoyl-Val-His, N-palmitoyl-Val-Trp, N-palmitoyl-Val-Asn, N-palmitoyl-Val-Arg, N-palmitoyl-Val-Lys, N-palmitoyl-Leu-His, N-palmitoyl-Leu-Trp, N-palmitoyl-Leu-Gln, N-palmitoyl-Leu-Asn, N-palmitoyl-Leu-Arg, N-palmitoyl-Leu-Lys, N-palmitoyl-Ile-His, N-palmitoyl-Ile-Trp, N-palmitoyl-Ile-Gln, N-palmitoyl-Ile-Asn, N-palmitoyl-Ile-Arg, N-palmitoyl-Ile-Lys, N-margaroyl-Gly-His, N-margaroyl-Gly-Trp, N-margaroyl-Gly-Gln, N-margaroyl-Gly-Asn, N-margaroyl-Gly-Arg, N-margaroyl-Gly-Lys, N-margaroyl-Ala-His, N-margaroyl-Ala-Trp, N-margaroyl-Ala-Gln, N-margaroyl-Ala-Asn, N-margaroyl-Ala-Arg, N-margaroyl-Ala-Lys, N-margaroyl-Val-His, N-margaroyl-Val-Trp, N-margaroyl-Val-Gln, N-margaroyl-Val-Asn, N-margaroyl-Val-Arg, N-margaroyl-Val-Lys, N-margaroyl-Leu-His, N-margaroyl-Leu-Trp, N-margaroyl-Leu-Gln, N-margaroyl-Leu-Asn, N-margaroyl-Leu-Arg, N-margaroyl-Leu-Lys, N-margaroyl-Ile-His, N-margaroyl-Ile-Trp, N-margaroyl-Ile-Gln, N-margaroyl-Ile-Asn, N-margaroyl-Ile-Arg, N-margaroyl-Ile-Lys, N-stearoyl-Gly-His, N-stearoyl-Gly-Trp, N-stearoyl-Gly-Gln, N-stearoyl-Gly-Asn, N-stearoyl-Gly-Arg, N-stearoyl-Gly-Lys, N-stearoyl-Ala-His, N-stearoyl-Ala-Trp, N-stearoyl-Ala-Gln, N-stearoyl-Ala-Asn, N-stearoyl-Ala-Arg, N-stearoyl-Ala-Lys, N-stearoyl-Val-His, N-stearoyl-Val-Trp, N-stearoyl-Val-Gln, N-stearoyl-Val-Asn, N-stearoyl-Val-Arg, N-stearoyl-Val-Lys, N-stearoyl-Leu-His, N-stearoyl-Leu-Trp, N-stearoyl-Leu-Gln, N-stearoyl-Leu-Asn, N-stearoyl-Leu-Arg, N-stearoyl-Leu-Lys, N-stearoyl-Ile-His, N-stearoyl-Ile-Trp, N-stearoyl-Ile-Asn, N-stearoyl-Ile-Arg, N-stearoyl-Ile-Lys, N-elaidoyl-Gly-His, N-elaidoyl-Gly-Trp, N-elaidoyl-Gly-Gln, N-elaidoyl-Gly-Asn, N-elaidoyl-Gly-Arg, N-elaidoyl-Gly-Lys, N-elaidoyl-Ala-His, N-elaidoyl-Ala-Trp, N-elaidoyl-Ala-Gln, N-elthdoyl-Ala-Asn, N-elaidoyl-Ala-Arg, N-elaidoyl-Ala-Lys, N-elaidoyl-Val-His, N-elaidoyl-Val-Trp, N-elaidoyl-Val-Gln, N-elaidoyl-Val-Asn, N-elaidoyl-Val-Arg, N-elaidoyl-Val-Lys, N-elaidoyl-Leu-His, N-elaidoyl-Leu-Trp, N-elaidoyl-Leu-Gln, N-elaidoyl-Leu-Asn, N-elaidoyl-Leu-Arg, N-elaidoyl-Leu-Lys, N-elaidoyl-Ile-His, N-elaidoyl-Ile-Trp, N-elaidoyl-Ile-Asn, N-elaidoyl-Ile-Arg, N-elaidoyl-Ile-Lys, N-arachidoyl-Gly-His, N-arachidoyl-Gly-Trp, N-arachidoyl-Gly-Gln, N-arachidoyl-Gly-Asn, N-arachidoyl-Gly-Arg, N-arachidoyl-Gly-Lys, N-arachidoyl-Ala-His, N-arachidoyl-Ala-Trp, N-arachidoyl-Ala-Gln, N-arachidoyl-Ala-Asn, N-arachidoyl-Ala-Arg, N-arachidoyl-Ala-Lys, N-arachidoyl-Val-His, N-arachidoyl-Val-Trp, N-arachidoyl-Val-Gln, N-arachidoyl-Val-Asn, N-arachidoyl-Val-Arg, N-arachidoyl-Val-Lys, N-arachidoyl-Leu-His, N-arachidoyl-Leu-Trp, N-arachidoyl-Leu-Gln, N-arachidoyl-Leu-Asn, N-arachidoyl-Leu-Arg, N-arachidoyl-Leu-Lys, N-arachidoyl-Ile-His, N-arachidoyl-Ile-Trp, N-arachidoyl-Ile-Gln, N-arachidoyl-Ile-Asn, N-arachidoyl-Ile-Arg, N-arachidoyl-Ile-Lys, N-behenoyl-Gly-His, N-behenoyl-Gly-Trp, N-behenoyl-Gly-Gln, N-behenoyl-Gly-Asn, N-behenoyl-Gly-Arg, N-behenoyl-Gly-Lys, N-behenoyl-Ala-His, N-behenoyl-Ala-Trp, N-behenoyl-Ala-Gln, N-behenoyl-Ala-Asn, N-behenoyl-Ala-Arg, N-behenoyl-Ala-Lys, N-behenoyl-Val-His, N-behenoyl-Val-Trp, N-behenoyl-Val-Gln, N-behenoyl-Val-Asn, N-behenoyl-Val-Arg, N-behenoyl-Val-Lys, N-behenoyl-Leu-His, N-behenoyl-Leu-Trp, N-behenoyl-Leu-Gln, N-behenoyl-Leu-Asn, N-behenoyl-Leu-Arg, N-behenoyl-Leu-Lys, N-behenoyl-Ile-His, N-behenoyl-Ile-Trp, N-behenoyl-Ile-Gln, N-behenoyl-Ile-Asn, N-behenoyl-Ile-Arg, and N-behenoyl-Ile-Lys.

Of the foregoing compounds, examples of more preferred lipopeptide compounds include N-lauroyl-Gly-His, N-lauroyl-Gly-Trp, N-lauroyl-Gly-Gln, N-lauroyl-Gly-Asn, N-lauroyl-Gly-Lys, N-lauroyl-Ala-His, N-lauroyl-Ala-Trp, N-lauroyl-Ala-Gln, N-lauroyl-Ala-Asn, N-lauroyl-Ala-Lys, N-lauroyl-Val-His, N-lauroyl-Val-Trp, N-lauroyl-Val-Gln, N-lauroyl-Val-Asn, N-lauroyl-Val-Lys, N-myristoyl-Gly-His, N-myristoyl-Gly-Trp, N-myristoyl-Gly-Gln, N-myristoyl-Gly-Asn, N-myristoyl-Gly-Lys, N-myristoyl-Ala-His, N-myristoyl-Ala-Trp, N-myristoyl-Ala-Gln, N-myristoyl-Ala-Asn, N-myristoyl-Ala-Lys, N-myristoyl-Val-His, N-myristoyl-Val-Trp, N-myristoyl-Val-Gln, N-myristoyl-Val-Asn, N-myristoyl-Val-Lys, N-palmitoyl-Gly-His, N-palmitoyl-Gly-Trp, N-palmitoyl-Gly-Gln, N-palmitoyl- Gly-Asn, N-palmitoyl-Gly-Lys, N-palmitoyl-Ala-His, N-palmitoyl-Ala-Trp, N-palmitoyl-Ala-Gln, N-palmitoyl-Ala-Asn, N-palmitoyl-Ala-Lys, N-palmitoyl-Val-His, N-palmitoyl-Val-Trp, N-palmitoyl-Val-Gln, N-palmitoyl-Val-Asn, N-palmitoyl-Val-Lys, N-margaroyl-Gly-His, N-margaroyl-Gly-Trp, N-margaroyl-Gly-Gln, N-margaroyl-Gly-Asn, N-margaroyl-Gly-Lys, N-margaroyl-Ala-His, N-margaroyl-Ala-Trp, N-margaroyl-Ala-Gln, N-margaroyl-Ala-Asn, N-margaroyl-Ala-Lys, N-margaroyl-Val-His, N-margaroyl-Val-Trp, N-margaroyl-Val-Gln, N-margaroyl-Val-Asn, N-margaroyl-Val-Lys, N-margaroyl-Gly-His, N-margaroyl-Gly-Trp, N-margaroyl-Gly-Gln, N-margaroyl-Gly-Asn, N-margaroyl-Gly-Lys, N-margaroyl-Ala-His, N-margaroyl-Ala-Trp, N-margaroyl-Ala-Gln, N-margaroyl-Ala-Asn, N-margaroyl-Ala-Lys, N-margaroyl-Val-His, N-margaroyl-Val-Trp, N-margaroyl-Val-Gln, N-margaroyl-Val-Asn, N-margaroyl-Val-Lys, N-stearoyl-Gly-His, N-stearoyl-Gly-Trp, N-stearoyl-Gly-Gln, N-stearoyl-Gly-Asn, N-stearoyl-Gly-Lys, N-stearoyl-Ala-His, N-stearoyl-Ala-Trp, N-stearoyl-Ala-Gln, N-stearoyl-Ala-Asn, N-stearoyl-Ala-Lys, N-stearoyl-Val-His, N-stearoyl-Val-Trp, N-stearoyl-Val-Gln, N-stearoyl-Val-Asn, N-stearoyl-Val-Lys, N-elaidoyl-Gly-His, N-elaidoyl-Gly-Trp, N-elaidoyl-Gly-Gln, N-elaidoyl-Gly-Asn, N-elaidoyl-Gly-Lys, N-elaidoyl-Ala-His, N-elaidoyl-Ala-Trp, N-elaidoyl-Ala-Gln, N-elaidoyl-Ala-Asn, N-elaidoyl-Ala-Lys, N-elaidoyl-Val-His, N-elaidoyl-Val-Trp, N-elaidoyl-Val-Gln, N-elaidoyl-Val-Asn, N-elaidoyl-Val-Lys, N-arachidoyl-Gly-His, N-arachidoyl-Gly-Trp, N-arachidoyl-Gly-Gln, N-arachidoyl-Gly-Asn, N-arachidoyl-Gly-Lys, N-arachidoyl-Ala-His, N-arachidoyl-Ala-Trp, N-arachidoyl-Ala-Gln, N-arachidoyl-Ala-Asn, N-arachidoyl-Ala-Lys, N-arachidoyl-Val-His, N-arachidoyl-Val-Trp, N-arachidoyl-Val-Gln, N-arachidoyl-Val-Asn, N-arachidoyl-Val-Lys, N-behenoyl-Gly-His, N-behenoyl-Gly-Trp, N-behenoyl-Gly-Gln, N-behenoyl-Gly-Asn, N-behenoyl-Gly-Lys, N-behenoyl-Ala-His, N-behenoyl-Ala-Trp, N-behenoyl-Ala-Gln, N-behenoyl-Ala-Asn, N-behenoyl-Ala-Lys, N-behenoyl-Val-His, N-behenoyl-Val-Trp, N-behenoyl-Val-Gln, N-behenoyl-Val-Asn, and N-behenoyl-Val-Lys.

Examples of the most preferred compounds include N-lauroyl-Ala-His, N-lauroyl-Ala-Trp, N-lauroyl-Gly-His, N-lauroyl-Gly-Gln, N-lauroyl-Gly-Asn, N-lauroyl-Gly-Lys, N-myristoyl-Gly-His, N-myristoyl-Gly-Gln, N-myristoyl-Gly-Asn, N-myristoyl-Gly-Lys, N-palmitoyl-Gly-His, N-palmitoyl-Gly-Gln, N-palmitoyl-Gly-Trp, N-palmitoyl-Gly-Gln, N-palmitoyl-Gly-Asn, N-palmitoyl-Gly-Lys, N-palmitoyl-Ala-His, N-palmitoyl-Ala-Trp, N-palmitoyl-Ala-Gln, N-palmitoyl-Ala-Asn, N-palmitoyl-Ala-Lys, N-palmitoyl-Val-His, N-palmitoyl-Val-Trp, N-palmitoyl-Val-Gln, N-palmitoyl-Val-Asn, N-palmitoyl-Val-Lys, N-margaroyl-Gly-His, N-margaroyl-Gly-Gln, N-margaroyl-Gly-Asn, N-margaroyl-Gly-Lys, N-margaroyl-Gly-His, N-margaroyl-Gly-Gln, N-margaroyl-Gly-Asn, N-margaroyl-Gly-Lys, N-stearoyl-Gly-His, N-stearoyl-Gly-Gln, N-stearoyl-Gly-Asn, N-stearoyl-Gly-Lys, N-elaidoyl-Gly-His, N-elaidoyl-Gly-Gln, N-elaidoyl-Gly-Asn, N-elaidoyl-Gly-Lys, N-arachidoyl-Gly-His, N-arachidoyl-Gly-Gln, N-arachidoyl-Gly-Asn, N-arachidoyl-Gly-Lys, N-behenoyl-Gly-His, N-behenoyl-Gly-Gln, N-behenoyl-Gly-Asn, and N-behenoyl-Gly-Lys.

Illustrative, non-limiting, examples of the base used in the reaction of the ester compound of formula (1) with the α-amino acid compound of formula (2) include alkali metals such as metallic sodium and metallic potassium; inorganic acid salts of alkali metals, such as sodium carbonate, potassium carbonate, potassium phosphate and sodium phosphate; alkali metal hydroxides such as sodium hydroxide and potassium hydroxide; alkali metal alkoxides such as sodium methoxide and potassium t-butoxide; fatty amines such as triethylamine and tri-n-butylamine; alicyclic amines such as 1,8-diazabicyclo[5.4.0]-7-undecene (hereinafter referred to as DBU) and 1,5-diazabicyclo[4.3.0]-5-nonene (hereinafter referred to as DBN); aromatic amines such as pyridine and 2-methyl-5-ethylpyridine; and alcohol solutions or alcohol dispersions of such base (solid) compounds. Any one of these may be used singly or two or more may be used in combination.

Of the above bases, from the standpoint of increasing the conversion and further enhancing the yield of the target substance, sodium methoxide, sodium ethoxide, potassium methoxide, potassium ethoxide, potassium t-butoxide, DBU or DBN is preferred. Sodium methoxide or an alcohol solution or alcohol dispersion of these metal alkoxides is preferred.

The sodium methoxide may be a solid, a methanol solution or a methanol dispersion, and may be prepared beforehand using metallic sodium and methanol or prepared within the reaction system and used. From the standpoint of ease of operation and yield, the use of a commercially available approximately 28% methanol solution of sodium methoxide is preferred.

The amount of base used, although not subject to any particular limitation, is typically about 1 to 10 equivalents, preferably 1 to 5 equivalents, and more preferably 1.3 to 2 equivalents, with respect to the compound of formula (1).

The nonpolar organic solvent included in the solvent used in the above reaction is not subject to any particular limitation; of the various types of solvents used in general organic synthesis, a solvent which exerts no influence on the reaction may be suitably selected and used.

Illustrative examples include saturated aliphatic hydrocarbon compounds such as pentane, c-pentane, hexane, c-hexane, methyl c-hexane, heptane, c-heptane, octane, decane and decalin; unsaturated aliphatic hydrocarbon compounds such as 1-hexene and 1-octyne; and aromatic hydrocarbon compounds such as benzene, toluene, xylene and o-dichlorobenzene. These solvents may be used singly or as combinations of two or more thereof.

Of these nonpolar organic solvents, in order to prevent hydrolysis of the ester compound of formula (1), increase the conversion and further improve the yield of the target product, the use of at least one selected from the group consisting of toluene, xylene, ortho-dichlorobenzene, pentane, hexane, heptane, octane, c-pentane, c-hexane, methyl c-hexane, c-heptane and 1-hexene is preferred, with c-hexane being especially preferred.

The solvent used in the reaction preferably includes an alcohol in addition to the above non-polar solvent. The alcohol used here is not subject to any particular limitation. Of the various types of alcohol solvents which are used in general organic synthesis, one which exerts no influence on the reaction may be suitably selected and used.

Illustrative examples include methanol, ethanol, n-propanol, i-propanol, n-butanol, i-butanol, s-butanol, t-butanol, n-pentanol, i-pentanol, s-pentanol, t-pentanol, n-hexanol, i-hexanol, s-hexanol, t-hexanol, octanol, decanol, ethylene glycol, 1,3-butanediol and glycerol. These solvents may be used singly or two or more thereof may be used in combination.

Of these solvents, in order to have the solvent dissolve the lipopeptide compound of formula (3) and the base and, under heated reaction conditions, uniformly mix with the above nonpolar organic solvent, and also in order to have a solution therein of the salt (e.g., an alkali metal salt) of the lipopeptide compound obtained as the product undergo, with cooling after the reaction, phase separation from the nonpolar organic solvent, the solvent is preferably at least one selected from the group consisting of methanol, ethanol, n-propanol, i-propanol, n-butanol, i-butanol, s-butanol and t-butanol. Methanol or ethanol is especially preferred.

The reaction between the ester compound of formula (1) and the α-amino acid compound of formula (2) may be carried out at any temperature up to the boiling points of the solvents used. However, to obtain the target product in a short time and a good yield, the temperature is preferably from 20 to 150° C., more preferably from 40 to 80° C., and even more preferably from 55 to 65° C.

The reaction time fluctuates depending on the reaction temperature, the base used and the type of organic solvent, and therefore cannot be strictly specified, but is generally from about 1 to about 48 hours.

The form of the reaction may be one where the reagents are all mixed at room temperature, then heated to the reaction temperature, or one where reaction control is carried out by dropwise addition of the necessary reagents. Alternatively, the reaction may be carried out in any of the following forms: in a batchwise manner, as a continuous reaction, under a vacuum, at normal pressure, or under an applied pressure. A reaction form that involves dropwise addition of the base at normal pressure is more preferred.

Following reaction completion, phase separation between the nonpolar organic solvent (top phase) and the alcohol solution phase of the lipopeptide compound salt obtained as the product (bottom phase) is effected by cooling, and the nonpolar organic solvent is removed by a liquid separating operation. Here, in terms of the ease of separation, an alkali metal salt is preferred as the lipopeptide compound salt.

Next, the product obtained is neutralized with a hydrogen halide, preferably in a solvent containing water and alcohol. For example, following reaction of the ester compound of formula (1) with the α-amino acid compound of formula (2), the nonpolar organic solvent is removed and the alcohol solution of lipopeptide compound salt that remains is neutralized by addition to a hydrogen halide solution.

The hydrogen halide employed in the neutralizing operation may generally be used, for ease of operation, in the form of an aqueous solution, and is exemplified by hydrochloric acid and hydrobromic acid. Hydrochloric acid is preferred.

During neutralization with a hydrogen halide, if the required amount necessary for neutralization is exceeded, a hydrochloride of the lipopeptide will end up forming, lowering the recovery of free form of lipopeptide. Hence, care must be taken in the amount of hydrogen halide used.

Following neutralization, crude product of the lipopeptide compound (free form) is collected by re-precipitation or the like, and work-up such as washing and recrystallization is carried out as needed to give a pure product.

The ester compound of formula (3) used in the present invention may be obtained by reacting a compound of formula (4) below with a compound of formula (5) below.

(4)

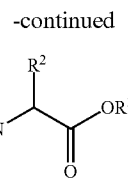

(5)

(where X, $R^1$, $R^2$ and $R^3$ are as defined above).

As mentioned above, in the preparation method of the present invention, following reaction completion, cooling the reaction solution brings about phase separation between the nonpolar organic solvent (top phase) and the alcohol solution phase of the lipopeptide compound salt obtained as the product (bottom phase). Hence, recovery and discarding of the nonpolar organic solvent by a liquid separating operation is easy.

Moreover, in cases where the lipopeptide compound has an ability to gel, polar solvents such as DMF which have hitherto been used in lipopeptide preparation tend to gel on account of the action by the lipopeptide after cooling. However, because gelling can be prevented by using a nonpolar organic solvent, this approach is highly useful in production.

Also, in this reaction, the solution becomes alkaline following the reaction. However, when an aqueous solution of hydrogen chloride is used in the amount required for neutralization, such neutralization reaches completion without the occurrence of gelling, enabling the product to be recovered in its free form. Crude crystals of the free form of product that have deposited out of solution are purified by a known technique such as recrystallization, enabling pure target product to be obtained.

In cases where neutralization is not carried out, by adding the alcohol solution of the lipopeptide compound salt (bottom phase) dropwise to an organic solvent, it is possible to re-precipitate and recover the lipopeptide compound salt as a solid.

EXAMPLES

The present invention is illustrated more fully below by way of synthesis examples, working examples and comparative examples, although the present invention is not limited by these examples.

As noted below, the reagents used in the following synthesis examples and other examples are commercially available reagents. The equipment indicated below was used to analyze the various compounds synthesized and to measure their physical properties.

Methanol: Kanto Chemical Co., Inc. (guaranteed)
Ethanol: Kanto Chemical Co., Inc. (extra pure)
Cyclohexane: Junsei Chemical Co., Ltd. (guaranteed)
Tetrahydrofuran: Kanto Chemical Co., Inc. (extra pure)
i-Propanol: Kanto Chemical Co., Inc. (extra pure)
N,N-Dimethylformamide (DMF): Kanto Chemical Co., Inc. (extra pure)
Toluene: Kanto Chemical Co., Inc. (extra pure)
Hexane: Kanto Chemical Co., Inc. (extra pure)
Heptane: Kanto Chemical Co., Inc. (extra pure)
Xylene: Kanto Chemical Co., Inc. (extra pure)
Palmitic acid chloride: Wako Pure Chemical Industries (extra pure, palmitoyl chloride), Aldrich (palmitoyl chloride), NOF Corporation (distilled palmitic acid chloride)
Glycine methyl ester hydrochloride: Tokyo Chemical Industry Co., Ltd.; Hamari Chemicals, Ltd.

Glycine ethyl ester hydrochloride: Tokyo Chemical Industry Co., Ltd.

Alanine methyl ester hydrochloride: Tokyo Chemical Industry Co., Ltd.

Leucine methyl ester hydrochloride: Tokyo Chemical Industry Co., Ltd.

Valine methyl ester hydrochloride: Tokyo Chemical Industry Co., Ltd.

Lauroyl chloride: Wako Pure Chemical Industries, Ltd.

Myristoyl chloride: Tokyo Chemical Industry Co., Ltd.

Stearoyl chloride: Tokyo Chemical Industry Co., Ltd.

L-Histidine: Tokyo Chemical Industry Co., Ltd., Kyowa Hakko Bio Co., Ltd.

L-Tryptophan: Kanto Chemical Co., Inc. (guaranteed)

Thionyl chloride: Wako Pure Chemical Industries, Ltd. (guaranteed)

Glycine: Wako Pure Chemical Industries, Ltd. (guaranteed)

Acetic anhydride: Wako Pure Chemical Industries, Ltd. (guaranteed)

Pivaloyl chloride: Kanto Chemical Co., Inc.

Sodium methoxide: Wako Pure Chemical Industries, Ltd. (extra pure)

Sodium methoxide, 28% methanol solution: Nippon Soda Co., Ltd. (liquid sodium methylate, 28%); Wako Pure Chemical Industries, Ltd. (28% sodium methoxide, methanol solution)

Sodium methoxide: Wako Pure Chemical Industries, Ltd. (extra pure)

Sodium hydroxide: Kanto Chemical Co., Inc. (extra pure)

Sodium carbonate: Junsei Chemical Co., Ltd. (extra pure)

Diethylamine: Junsei Chemical Co., Ltd. (extra pure)

Triethylamine: Tokyo Chemical Industry Co., Ltd.

Hydrochloric acid: Kanto Chemical Co., Inc. (extra pure)

Acetic acid: Junsei Chemical Co., Ltd. (guaranteed)

Succinic acid: Junsei Chemical Co., Ltd. (guaranteed)

Phosphoric acid: Junsei Chemical Co., Ltd. (extra pure)

Sodium phosphate, monobasic: Wako Pure Chemical Industries, Ltd.

Trifluoroacetic acid: Kanto Chemical Co., Inc. (extra pure)

NMR: JNM-ECP300 (manufactured by JEOL Ltd.)

Melting point: Automated melting point apparatus FP-62 (manufactured by Mettler Toledo KK)

pH meter: AS-212 (manufactured by Horiba, Ltd.)

IR: Nicolet 6700/Nicolet Cotiniuum (manufactured by Thermo FISHER SCIENTIFIC)

The HPLC analysis conditions are shown below.

HPLC Conditions (1)

Column: Inertsil ODS-3 (manufactured by GL Sciences)

Developing solvent: MeOH/phosphate buffer (pH=2.1)=85/15 (volumetric ratio)

Method of preparing phosphate buffer (pH=2.1): Water was added to 7.8 g (50 mmol) of monobasic sodium phosphate ($NaH_2PO_4 \cdot 2H_2O$) and 3.4 mL (50 mmol) of 85% phosphoric acid so as to bring the total volume up to 1 liter.

Oven temperature: 40° C.

Method of detection: UV, 205 nm; and RID

Flow rate: 2.0 mL/min

Amount of injection: 20 μL

Retention time: N-palmitoyl-Gly-His, 5.5 min; N-palmitoyl-Gly, 9.3 min; N-palmitoyl-Gly-methyl, 11.2 min; N-palmitoyl-Gly-ethyl, 11.4 min HPLC Conditions (2): Example 21 only Column: CHIRALPAK® IC (manufactured by Daicel Chemical Industries, Ltd.)

Developing solvent: Hexane/ethanol/trichloroacetic acid/diethylamine=90/10/0.1/0.1 (volumetric ratio)

Oven temperature: 25° C.

Method of detection: UV, 205 nm

Flow rate: 1.0 mL/min

Amount of injection: 10 μL

Retention time: N-palmitoyl-Gly-His, L-form: 9.5 min; D-form: 10.9 min

Example 1

Synthesis of N-Palmitoyl-Gly-Methyl

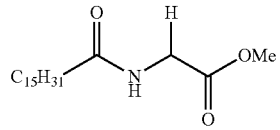

A 2 L four-neck flask was charged with 89.1 g (709 mmol) of glycine methyl ester hydrochloride, 75.2 g (709 mmol) of sodium carbonate (base), 750 g of water and 450 g of toluene (organic solvent), and stirred. Next, a solution obtained by dissolving 150 g (546 mmol) of palmitic acid chloride in 900 g of toluene was added dropwise thereto over a period of 2 hours at a reaction temperature of 25±5° C., whereupon a white solid precipitated out, forming a slurry. Two hours of stirring at 25° C. was followed by the addition of another 750 g of water and 1 hour of stirring, then filtration, and washing with 150 g of water. The resulting wet product was dried under reduced pressure, giving 150.61 g (purity, 99.8%; yield, 87%) of white crystals of N-palmitoyl-Gly-methyl.

$^1$H-NMR (300 MHz, MeOH-$d_4$, δ ppm): 3.97 (2H, s), 3.71 (3H, s), 2.23 (2H, t, J=7.4 Hz), 1.61 (2H, m), 1.28 (24H, m), 0.89 (3H, t, J=6.8 Hz)

MS (ESI) m/z: 327.78 ($M^1$).

Melting point: 78.1° C. (N=3)

Example 2

Synthesis of Free form of N-Palmitoyl-Gly-His

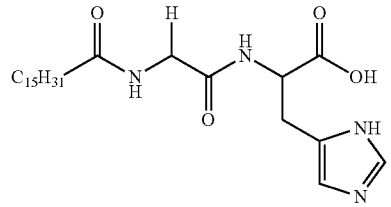

A 2 L four-neck flask was charged with 28.4 g (183 mmol) of L-histidine, 60 g (183 mmol) of N-palmitoyl-Gly-methyl and 600 g of cyclohexane, following which the flask contents were stirred under heating on an oil bath. The moment that the reaction mixture reached 60° C., the dropwise addition of 70.7 g (366 mmol) of a 28% methanol solution of sodium methoxide (base) was started, with addition being completed in 20 minutes. Following the completion of addition, stirring was continued for 1 hour at about 60° C.

Next, the oil bath was removed and the reaction system was allowed to cool to 25° C., resulting in separation of the system into a top phase composed primarily of cyclohexane and a bottom phase composed primarily of methanol. Using a separatory funnel, the bottom phase of the reaction mixture that had separated into two phases was collected in an Erlenmeyer flask. A solution obtained by mixing together 180 g of water and 420 g of methanol was added to the remaining top phase, and the solution that separated again into two phases was left at rest for 20 minutes, following which the bottom phase was collected in an Erlenmeyer flask and mixed with the bottom phase collected earlier.

This mixed solution was added to a mixed solution composed of 720 g of water, 780 g of ethanol and 36.5 mL of 6N hydrochloric acid (366 mmol, 1 equivalent with respect to the above base) while stirring at 25° C. After addition of the entire amount was completed, the reaction mixture was heated to 60° C. and stirred for 1 hour. The reaction mixture was then allowed to cool to 25° C., and the solid that deposited out was collected by filtration and washed with 180 g of water.

Next, 900 g of water and 1,800 g of methanol were added to the solid, and heated and stirred for 1 hour at 60° C., following which the solid that deposited out when the system was left to cool to 25° C. was collected by filtration. The same operations were repeated one more time, after which the solid thus obtained was dried under reduced pressure. Next, 650 g of tetrahydrofuran was added to the dried solid, and stirring was carried out for 1 hour at 25° C. The solid was subsequently collected by filtration, then 1,300 g of methanol and 650 g of tetrahydrofuran were added to the solid thus obtained and dissolved under heating at 60° C., following which the system was cooled to 0° C. over a period of 2 hours and the final liquid was stirred overnight at 0° C. The solid that deposited out was collected by filtration and dried under reduced pressure, thereby giving 60.0 g (yield, 72.8%) of white crystals of free form of N-palmitoyl-Gly-His.

$^1$H-NMR (300 MHz, DMSO-$d_6$, δ ppm): 8.12 (1H, d, J=7.8 Hz), 8.06 (1H, t, J=5.7 Hz), 7.56 (1H, s), 6.81 (1H, s), 4.38 (1H, q, J=7.8 Hz), 3.69 (2H, dd, J=5.7 Hz and J=10.2 Hz), 2.89 (2H, m), 2.20 (2H, t, J=6.9 Hz), 1.48 (2H, m), 1.23 (24H, s), 0.85 (3H, t, J=7.2 Hz)

MS (EI) m/z: 451.43 ($M^+$+1, bp)

Melting point: Not observed

Example 3

Synthesis of Free form of N-Palmitoyl-Gly-His

Free form of N-palmitoyl-Gly-His was synthesized by a substantially similar method as in Example 2 using 10.3 kg (31.45 mol) of N-palmitoyl-Gly-methyl, giving 9.02 kg (yield, 63.6%) of the product.

Example 4

Synthesis of Sodium Salt of N-Palmitoyl-Gly-His

A 200 mL four-neck flask was charged with 9.0 g (27.5 mmol) of N-palmitoyl-Gly-methyl, 4.3 g (27.5 mmol) of L-histidine and 90 g of the organic solvent cyclohexane, and the temperature was raised to 60° C. under stirring. Next, a 28% methanol solution of sodium methoxide as the base was added dropwise thereto over a period of 15 minutes, and the reaction was carried out for 1 hour at 60±5° C. Following reaction completion, the system was cooled to 35° C. or below, and the methanol phase of the solution which separated into a cyclohexane phase and a methanol phase was re-precipitated in 270 g of hexane, causing crystals to deposit out. This solution was cooled to 0° C. and stirred for 1 hour, following which filtration was carried out. The wet product thus obtained was dried under reduced pressure, thereby giving 10 g of light yellow crystals of the sodium salt of N-palmitoyl-Gly-His (purity, 94%; yield, 77%).

Examples 5 to 12

N-Palmitoyl-Gly-His was synthesized using the same starting compound as in Example 2, but changing the solvents, base, reaction temperature and reaction time as shown in Table 1. Table 1 also shows the conversions in HPLC (RID detector) and the relative area percentages of the target compounds.

TABLE 1

| Example | Solvent | Base | Conversion[1] (%) | RID Area % | | |
|---|---|---|---|---|---|---|
| | | | | Target product[2] | Hydrolysate[3] | Starting compound[4] |
| 5 | Toluene | NaOEt | 92 | 64 | 28 | 8 |
| 6 | Toluene | KOMe | 100 | 71 | 29 | 0 |
| 7 | Toluene | NaOMe | 98 | 80 | 18 | 2 |
| 8 | Xylene | NaOMe | 97 | 76 | 21 | 3 |
| 9 | Heptane | NaOMe | 100 | 92 | 8 | 0 |
| 10 | Heptane:toluene = 5:5 (wt/wt) | NaOMe | 92 | 85 | 7 | 8 |
| 11 | Heptane:toluene = 7:3 (wt/wt) | NaOMe | 97 | 89 | 8 | 3 |
| 12 | Cyclohexane | NaOMe | 99 | 93 | 6 | 1 |

[1]Method of calculating conversion (%) = (Area % of target compound + Area % of hydrolyzate)/(Area % of target compound + Area % of hydrolyzate + Area % of starting compound)

[2]Target compound: N-palmitoyl-Gly-His

[3]Hydrolyzate: N-palmitoyl-Gly

[4]Starting compound: N-palmitoyl-Gly-methyl

Comparative Example 1

Aside from changing the solvent to DMF and setting the reaction temperature to 80° C., the reaction was carried out under the same conditions as in Example 2. However, the reaction did not reach completion and, after cooling, the reaction system gelled. In addition, the hydrolyzate increased, as a result of which the yield fell to 65%.

Examples 13 to 19

Aside from adjusting the pH at the time of neutralization as shown in Table 2, the synthesis of free form of N-palmitoyl-Gly-His was carried out by the same procedure as in Example 2. Changes in the filtrate loss value were confirmed.

TABLE 2

| Example | Supernatant pH | Filtrate loss (%) |
|---|---|---|
| 13 | 7.6 | 12 |
| 14 | 7.2 | 4 |
| 15 | 7.0 | 4 |
| 16 | 6.7 | 1 |
| 17 | 6.6 | 2 |
| 18 | 6.4 | 0.8 |
| 19 | 6.2 | 0.2 |

Example 20

Comparative Examples 2 to 8

Aside from changes, as shown in Table 3, in the types and amounts of acids used for neutralization following the reaction, synthesis was carried out in the same way as in Example 2. However, in Comparative Examples 2 to 8, recovering N-palmitoyl-Gly-His was difficult. IR charts of the resulting N-palmitoyl-Gly-His products are shown in FIGS. 1 to 8.

TABLE 3

Figure 2:
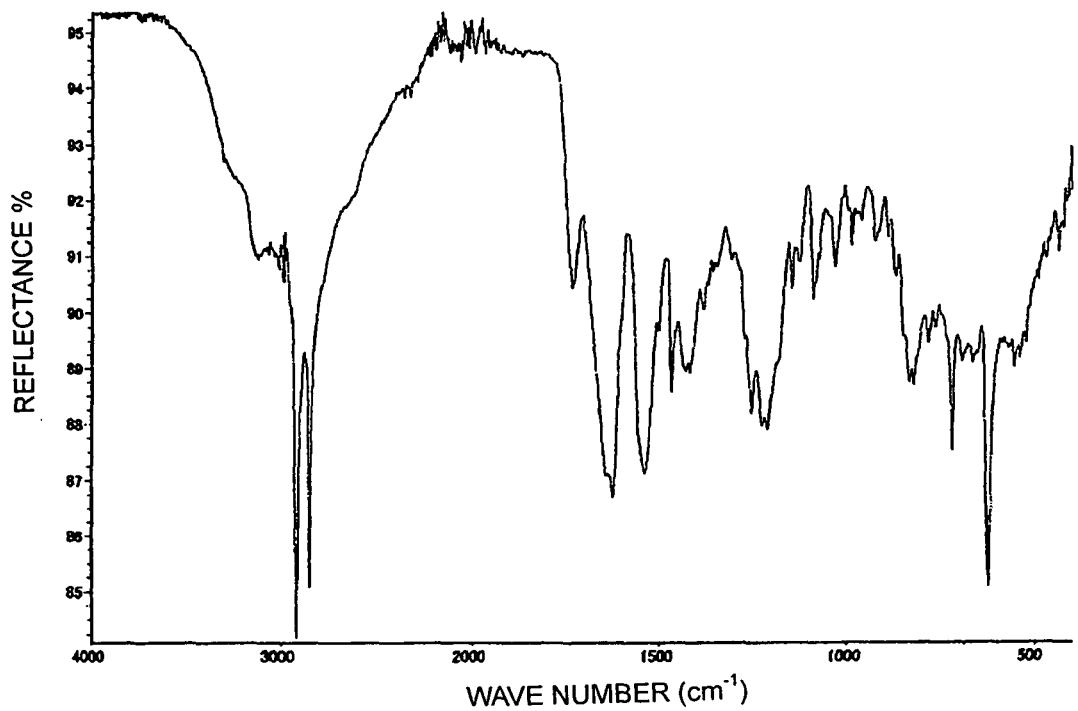
FIG. 2 shows the IR spectrum of the N-palmitoyl-Gly-His obtained in Comparative Example 2.
Figure 3:
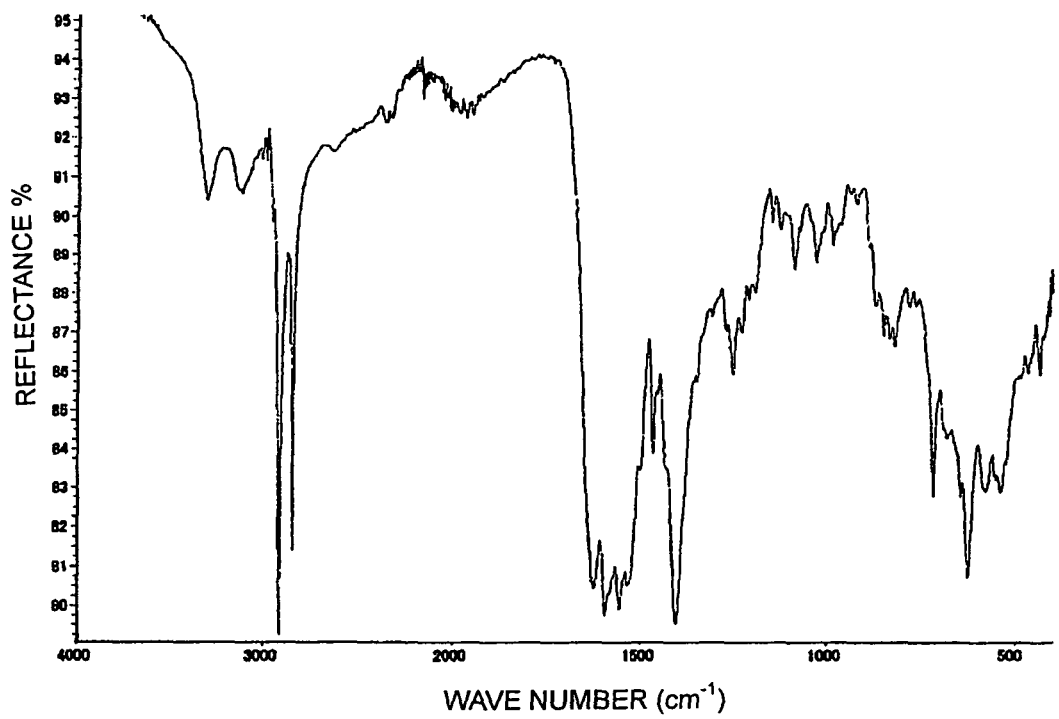
FIG. 3 shows the IR spectrum of the N-palmitoyl-Gly-His obtained in Comparative Example 3.
Figure 4:
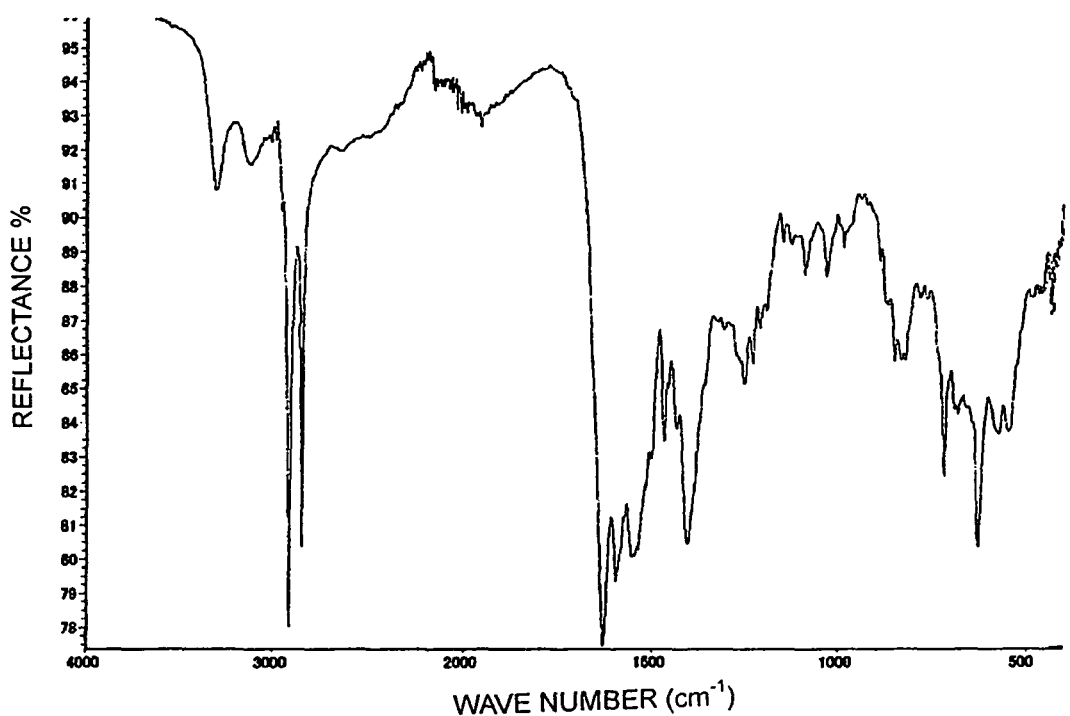
FIG. 4 shows the IR spectrum of the N-palmitoyl-Gly-His obtained in Comparative Example 4.
Figure 5:
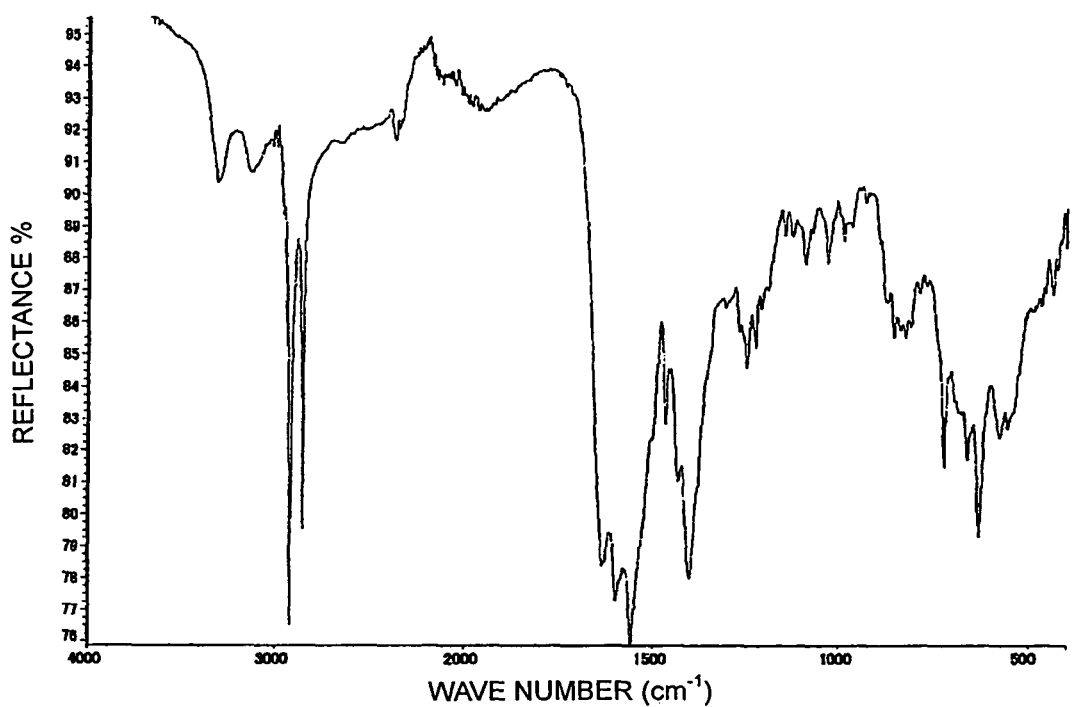
FIG. 5 shows the IR spectrum of the N-palmitoyl-Gly-His obtained in Comparative Example 5.
Figure 6:
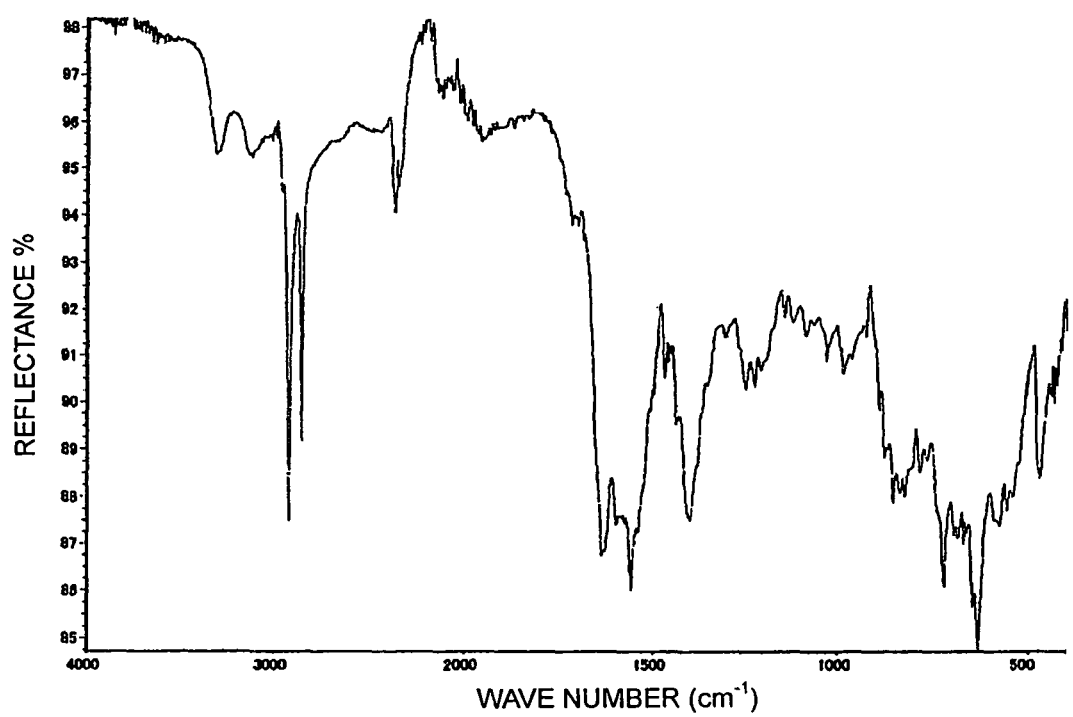
FIG. 6 shows the IR spectrum of the N-palmitoyl-Gly-His obtained in Comparative Example 6.
Figure 7:
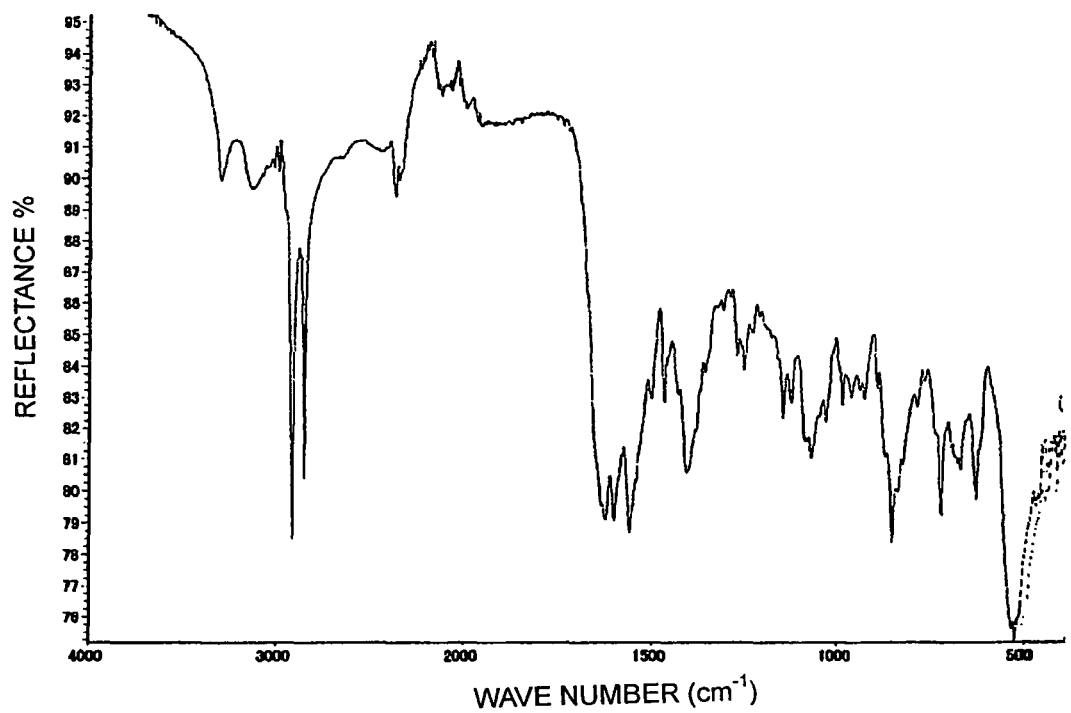
FIG. 7 shows the IR spectrum of the N-palmitoyl-Gly-His obtained in Comparative Example 7.
Figure 8:
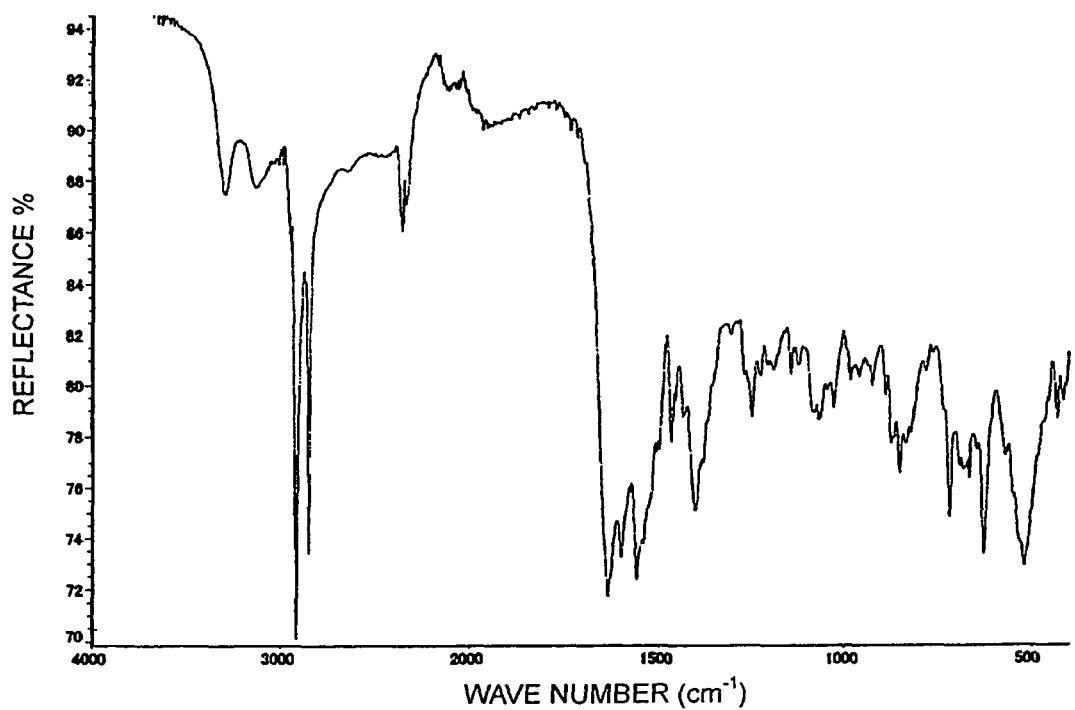
FIG. 8 shows the IR spectrum of the N-palmitoyl-Gly-His obtained in Comparative Example 8.

| | Acid/ equivalents (total) | Condition at time of neutralization | IR |
|---|---|---|---|
| EX 20 | Hydrochloric acid/2.0 eq. | Free form deposited out as a solid | [FIG. 1] (Solid obtained was dried and measured) |
| CE 2 | Hydrochloric acid/4.0 eq. | Solid became a hydrochloride and re-dissolved | [FIG. 2] (Re-dissolved solution was dried to hardness and measured) |
| CE 3 | Acetic acid/2.0 eq. | Gelled and could not be drawn from reactor | [FIG. 3] (Gel was scraped out, dried, and measured) |
| CE 4 | Acetic acid/4.0 eq. | Gelled and could not be drawn from reactor | [FIG. 4] (Gel was scraped out, dried, and measured) |
| CE 5 | Succinic acid/1.0 eq. | Gelled and could not be drawn from reactor | [FIG. 5] (Gel was scraped out, dried, and measured) |
| CE 6 | Succinic acid/1.5 eq. | Gelled and could not be drawn from reactor | [FIG. 6] (Gel was scraped out, dried, and measured) |
| CE 7 | Phosphoric acid/1.0 eq. | Gelled and could not be drawn from reactor | [FIG. 7] (Gel was scraped out, dried, and measured) |
| CE 8 | Phosphoric acid/1.5 eq. | Gelled and could not be drawn from reactor | [FIG. 8] (Gel was scraped out, dried, and measured) |

Comparative Example 9

Aside from changing the mixed solution of acid used for neutralization following the reaction to an aqueous solution obtained by adding hydrochloric acid to water (2 equivalents with respect to the base), synthesis was carried out in the same way as in Example 2. However, when neutralization and re-precipitation were carried out, the reaction system gelled and could not be drawn from the reactor.

Example 21

As in Example 2, N-palmitoyl-Gly-methyl and L-histidine were reacted in cyclohexane and at 60° C. using a 28% methanol solution of sodium methoxide as the base, following which neutralization and purification were carried out, giving free form of N-palmitoyl-Gly-His.

Figure 9:
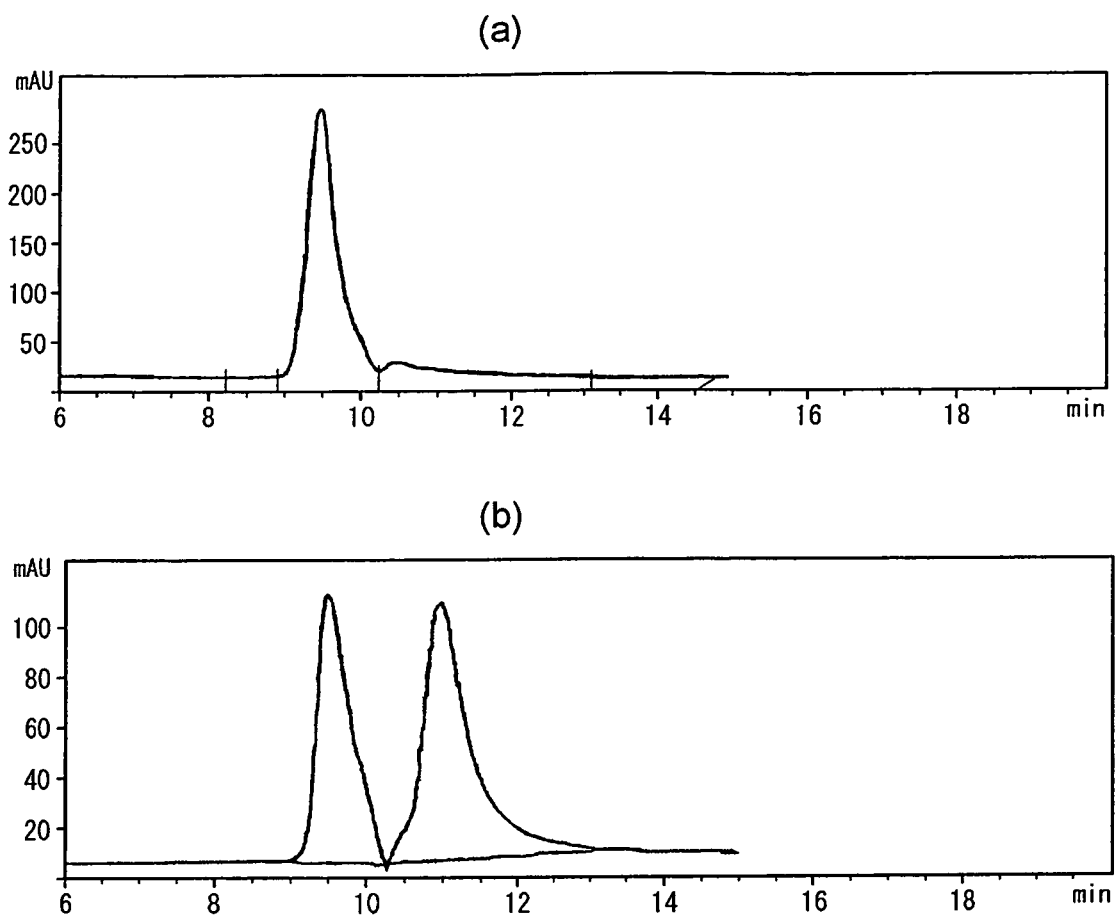
FIG. 9 shows the HPLC spectrum of the free form of N-palmitoyl-Gly-His (FIG. 9A) and the high performance liquid chromatography (HPLC) spectrum of free form of racemic N-palmitoyl-Gly-His (FIG. 9B) obtained in Example 21.

Upon checking the HPLC spectrum of the resulting free form of N-palmitoyl-Gly-His (under HPLC Conditions (2), see FIG. 9), racemization was not confirmed. FIG. 9A shows the HPLC spectrum of the free form of N-palmitoyl-Gly-His obtained in this example (using L-histidine), and FIG. 9B shows the HPLC spectrum of the free form of N-palmitoyl-Gly-His obtained using racemic histidine.

Synthesis of N-Palmitoyl-Gly-His from N-Palmitoyl-Gly

Synthesis Example 1

Synthesis of N-Palmitoyl-Gly

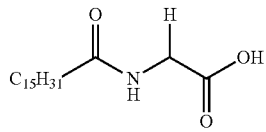

First, 27.3 g (364 mmol) of glycine and 29.1 g (727 mmol) of sodium hydroxide were dissolved in a mixed solvent of 450 g composed of i-propanol and 200 g of water under stirring at room temperature, then cooled to 10° C. Next, 100 g (364 mmol) of palmitic acid chloride was added dropwise thereto over a period of 1 hour. The reaction product was returned to room temperature, then stirred for about 15 hours. Next, 400 g of water was added thereto, following which 73.8 g (727 mmol) of 35% hydrochloric acid was added dropwise. The solid that deposited out was recovered, slurry washed, and purified by re-crystallization from methanol, giving 36.4 g (yield, 32%) of N-palmitoyl-Gly as a white solid.

$^1$H-NMR (300 MHz, DMSO-$d_6$, δ ppm): 12.43 (1H, brs), 8.07 (1H, t, J=5.7 Hz), 3.70 (2H, d, J=5.7 Hz), 2.09 (2H, t, J=7.8 Hz), 1.47 (2H, m), 1.23 (24H, brs), 0.85 (3H, t, J=6.9 Hz).

Melting point: 125.0° C. (N=3)

Comparative Example 10

Using thionyl chloride, N-palmitoyl-Gly was converted to the acid chloride in toluene at room temperature, then reacted with L-histidine using triethylamine as the base. However, only a trace amount of N-palmitoyl-Gly-His formed.

Comparative Example 11

N-Palmitoyl-Gly was reacted with acetic anhydride in toluene at 80° C. and thereby acetylated, and was subsequently reacted with L-histidine at 70° C. in the DMF, using triethylamine as the base. However, N-palmitoyl-Gly-His did not form.

Comparative Example 12

In the presence of triethylamine as the base, N-palmitoyl-Gly was reacted with pivaloyl chloride in toluene at 0° C., thereby generating an acid anhydride in the system, following which more triethylamine was added and reaction was carried out with L-histidine. However, N-palmitoyl-Gly-His did not form.

Example 22

Synthesis of N-Palmitoyl-Gly-Ethyl

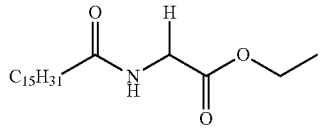

A 300 mL four-neck flask was charged with 6.6 g (47.3 mmol) of glycine ethyl ester hydrochloride, 5.0 g (47.3 mmol) of sodium carbonate as the base, 50 g of water and 30 g of toluene as the organic solvent, and the flask contents were stirred. Next, a solution of 10 g (36.4 mmol) of palmitic acid chloride dissolved in 60 g of toluene was added dropwise thereto over a period of 2 hours at a reaction temperature of 25±5° C., whereupon a white solid deposited out, forming a slurry. The slurry was stirred at 25° C. for 1 hour, following which another 50 g of water was added and stirring was carried out for 1 hour. The flask contents were then filtered and washed with 30 g of water. The resulting wet product was dried under reduced pressure, giving 7.0 g of white crystals of N-palmitoyl-Gly-ethyl (yield, 56%).

$^1$H-NMR (300 MHz, CDCl$_3$, δ ppm): 6.02-5.86 (m, 1H), 4.22 (2H, q, J=7.2 Hz), 4.03 (2H, d, J=5.4 Hz), 2.23 (2H, t, J=8.1 Hz), 1.72-1.56 (2H, m), 1.34-1.22 (27H, m), 0.89 (3H, t, J=6.6 Hz)

MS (ESI) m/z: 342.37 (M+H)$^+$.

Melting point: 110.0° C. (N=3)

Example 23

Synthesis of Free form of N-Palmitoyl-Gly-His

A 100 mL four-neck flask was charged with 0.91 g (5.8 mmol) of L-histidine, 2.0 g (5.8 mmol) of N-palmitoyl-Gly-ethyl and 20 g of cyclohexane, then 2.2 g (11.6 mmol) of a 28% methanol solution of sodium methoxide as the base was added, and the flask contents were heated under stirring to 60° C. on an oil bath. Stirring was continued for 1 hour at about 60° C.

Next, the oil bath was removed and the solution was allowed to cool to 25° C. The solution was added, at 25° C. and under stirring, to a mixed solution of 30 g of water, 40 g of methanol and 1.9 mL (11.6 mmol) of 6N hydrochloric acid. After addition of the entire amount was completed, the reaction solution was heated to 60° C. and stirred for 1 hour. The reaction solution was then allowed to cool to 25° C., and the solid that deposited out was collected by filtration and washed with 6 g of water. The solid thus obtained was dried under reduced pressure.

Next, 20 g of tetrahydrofuran and 40 g of methanol were added to the dried solid, and the solution was stirred at 60° C. for 1 hour. The 60° C. mixed solution was then added dropwise to 20 g of tetrahydrofuran that had been cooled to 0° C. At this time, addition was carried out gradually such that the upper limit in the temperature on the side being added to was 15° C. Following the completion of dropwise addition, the system was aged for 10 minutes at 0° C., and the solid was collected by filtration and dried under reduced pressure, giving 1.1 g (yield, 41%) of white crystals of free form of N-palmitoyl-Gly-His.

Example 24

Synthesis of Free form of N-Palmitoyl-Gly-Trp

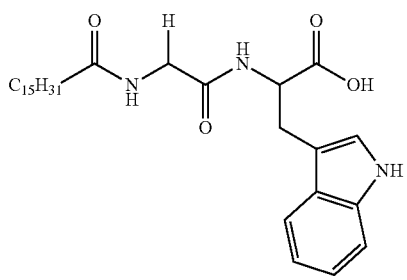

A 100 mL four-neck flask was charged with 1.25 g (6.1 mmol) of L-tryptophan, 2.0 g (6.1 mmol) of N-palmitoyl-Gly-methyl, 20 g of cyclohexane and 0.8 g of methanol, and stirred under heating at 60° C. on an oil bath. Next, 2.4 g (12.2 mmol) of a 28% methanol solution of sodium methoxide as the base was added, and stirring was continued for 2 hours at about 60° C. The oil bath was then removed, 0.4 g of methanol was added and, after being allowed to cool to 25° C., this solution was added, at 25° C. and under stirring, to a mixed solution composed of 30 g of water, 40 g of methanol and 2.0 mL (12.2 mmol) of 6N hydrochloric acid. After addition of the entire amount had been completed, the reaction solution was heated to 60° C. and stirred for 1 hour. The solution was then allowed to cool to 25° C. and the solid that deposited out was collected by filtration and washed with 6 g of water. Next, 30 g of water and 40 g of methanol were added to the resulting solid, and the system was heated to 60° C. and stirred for 1 hour. The system was then allowed to cool to 25° C. and the solid that deposited out was collected by filtration and washed with 6 g of water. The resulting solid was dried under reduced pressure, thereby giving 2.3 g (yield, 74%; purity, 90%) of white crystals of free form of N-palmitoyl-Gly-Trp.

$^1$H-NMR (300 MHz, DMSO-d$_6$, δ ppm): 10.76 (1H, s), 7.98 (1H, t, J=6.0 Hz), 7.74 (1H, d, J=7.2 Hz), 7.51 (1H, d, J=7.5 Hz), 7.29 (1H, d, J=7.5 Hz), 7.08 (1H, s), 7.02 (1H, d, J=7.5 Hz), 6.93 (1H, d, J=7.5 Hz), 4.31 (1H, q, J=7.8 Hz), 3.84-3.50 (2H, m), 3.17 (1H, dd, J=5.4 Hz, J=5.4 Hz), 3.01 (1H, dd, J=6.6 Hz, J=6.6 Hz), 2.07 (2H, t, J=6.9 Hz), 1.55-1.35 (2H, m), 1.35-1.25 (24H, m), 0.85 (3H, t, J=6.9 Hz)

MS (ESI) m/z: 500.2 (M+H)$^+$.

Melting point: 159.6° C. (N=4)

Example 25

Synthesis of N-Lauroyl-Ala-Methyl

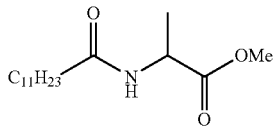

A 500 mL four-neck flask was charged with 16.6 g (118.9 mmol) of L-alanine methyl ester hydrochloride, 12.6 g (118.9 mmol) of sodium carbonate as the base, 100 g of water and 60 g of toluene as the organic solvent, following which the flask contents were stirred. A solution of 20 g of lauroyl chloride (91.4 mmol) dissolved in 120 g of toluene was added dropwise thereto at a reaction temperature of 25±5° C. over a period of 1 hour. After 2 hours of stirring at 25° C., another 200 g of water was added, and stirring was continued for 1 hour. The organic phase was separated off, concentrated under reduced pressure and dried in vacuo, thereby giving a white solid. The resulting solid was suspended and stirred for 2 hours in 250 g of water, following which filtration and drying were carried out, giving 24.7 g (yield, 94.5%) of white crystals of N-lauroyl-Ala-methyl.

$^1$H-NMR (300 MHz, CDCl$_3$, δ ppm): 6.02 (1H, s), 4.61 (1H, t, J=7.3 Hz), 3.75 (3H, s), 2.23-2.17 (3H, m), 1.26-1.41 (20H, m), 0.88 (3H, t, J=6.6 Hz)

MS (ESI) m/z: 286.1 (M+H)$^+$.

Example 26

Synthesis of Free form of N-Lauroyl-Ala-His

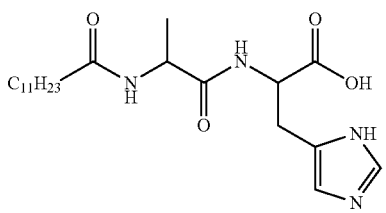

A 200 mL four-neck flask was charged with 3.81 g (24.5 mmol) of L-histidine, 7.0 g (24.5 mmol) of N-lauroyl-Ala-methyl, 70 g of cyclohexane and 2.8 g of methanol, and the flask contents were stirred under heating at 60° C. on an oil bath. Next, 9.5 g (49.0 mmol) of a 28% methanol solution of sodium methoxide as the base was added, and stirring was continued for 2 hours at about 60° C. The oil bath was then removed and 1.4 g of methanol was added to the flask, the system was allowed to cool to 25° C., and this solution was added under stirring at 25° C. to a mixed solution composed of 84 g of water, 91 g of methanol and 8.0 mL (49.0 mmol) of 6N hydrochloric acid. After addition of the entire amount was completed, the reaction solution was heated to 60° C. and stirred for 1 hour. Next, the solution was allowed to cool to 25° C. and concentrated, thereby giving a clay-like solid. The resulting solid was charged into a mixed solvent composed of 35 g of toluene and 35 g of methanol, suspended at 50° C., and the insolubles were removed by filtration under heating. The resulting filtrate was concentrated and dried under reduced pressure, giving 7.9 g (yield, 79%) of light brown crystals of free form of N-lauroyl-Ala-His.

$^1$H-NMR (300 MHz, DMSO-d$_6$, δ ppm): 8.02 (1H, dd, J1=12.3 Hz, J2=7.8 Hz), 7.9 (1H, dd, J1=12.4 Hz, J2=7.2 Hz), 7.50 (1H, t, J=1.2 Hz), 6.74 (1H, d, J=5.8 Hz), 4.24 (2H, dd, J1=14.6 Hz, J2=7.2 Hz), 2.80-2.96 (2H, m), 1.09-1.47 (23H, m), 0.85 (3H, t, J=6.3 Hz)

MS (ESI) m/z: 409.0 (M−H)$^-$.

Example 27

Synthesis of Free form of N-Lauroyl-Ala-Trp

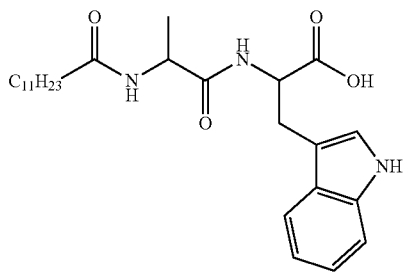

A 100 mL four-neck flask was charged with 5.0 g (24.5 mmol) of L-tryptophan, 7.0 g (24.5 mmol) of N-lauroyl-Ala-methyl, 70 g of cyclohexane and 2.8 g of methanol, and the flask contents were stirred under heating at 60° C. on an oil bath. Next, 9.5 g (49.0 mmol) of a 28% methanol solution of sodium methoxide as the base was added, and stirring was continued for 2 hours at about 60° C. The oil bath was then removed, 1.4 g of methanol was added, and the solution was allowed to cool to 25° C. This solution was added, under stirring at 35° C., to a mixed solution composed of 84 g of water, 91 g of methanol and 8.2 mL (49.0 mmol) of 6N hydrochloric acid. The pH was set to 6.7 by adding a 0.1N aqueous sodium hydroxide solution, following which the solvent was driven off by concentration under reduced pressure. Ethyl acetate and water were added to the residue, and the aqueous phase was extracted with ethyl acetate. The aqueous phase was concentrated under a reduced pressure to drive off the water and effect drying, thereby giving 9.2 g (yield, 83%; purity, 99%) of white crystals of free form of N-lauroyl-Ala-Trp.

$^1$H-NMR (300 MHz, DMSO-d$_6$, δ ppm): 10.75 (1H, s), 8.01 (1H, t, J=7.8 Hz), 7.58-6.89 (5H, m), 4.22 (2H, m), 3.48-2.94 (2H, m), 2.06 (2H, t, J=5.4 Hz), 1.44 (2H, brs), 1.22-1.11 (16H, m), 1.05 (2H, d, J=7.2 Hz), 0.85 (3H, t, J=6.9 Hz)

MS (ESI) m/z: 456.5 (M−H)$^-$.

Example 28

Synthesis of N-Lauroyl-Gly-Methyl

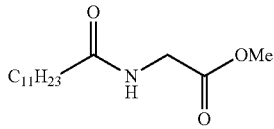

A 500 mL four-neck flask was charged with 16.4 g (130.7 mmol) of glycine methyl ester hydrochloride, 13.9 g (201.1 mmol) of sodium carbonate as the base, 110 g of water and 66 g of toluene as the organic solvent, and the flask contents were stirred. Next, a solution of 22 g (100.6 mmol) of lauroyl chloride dissolved in 132 g of toluene was added dropwise thereto over a period of 1 hour at a reaction temperature of 25±5° C. After 2 hours of stirring at 25° C., another 100 g of water was added and stirring was continued for 1 hour. The organic phase was separated off, concentrated under reduced pressure and dried in vacuo, giving 27.3 g (yield, 100%) of white crystals of N-lauroyl-Gly-methyl.

$^1$H-NMR (300 MHz, CDCl$_3$, δ ppm): 5.91 (s, 1H), 4.05 (d, J=5.2 Hz, 2H), 3.77 (s, 3H), 2.24 (t, J=7.6 Hz, 2H), 1.65-1.25 (m, 18H), 0.88 (t, J=6.7 Hz, 3H)

MS (API) m/z: 272.0 (M+H)$^+$.

Melting point: 62.5° C.

Example 29

Synthesis of Free form of N-Lauroyl-Gly-His

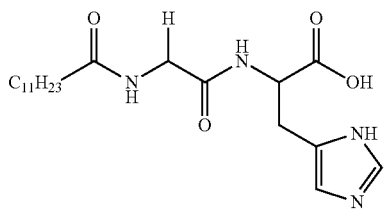

A 500 mL four-neck flask was charged with 11.4 g (73.7 mmol) of L-histidine, 20.0 g (73.7 mmol) of N-lauroyl-Gly-methyl, 200 g of cyclohexane and 8.0 g of methanol, and the flask contents were stirred under heating at 60° C. on an oil bath. Next, 28.4 g (147.4 mmol) of a 28% methanol solution of sodium methoxide as the base was added, and stirring was continued for 2 hours at about 60° C. The reaction solution was then cooled to about 50° C., and a mixed solution composed of 24 g of water, 26 g of methanol and 2.5 g (14.7 mmol) of 6N hydrochloric acid was added. Next, the solution was cooled to 25° C. and added, at 25° C. and under stirring, to a mixed solution composed of 216 g of water, 234 g of methanol, and 22.5 g (132.7 mmol) of 6N hydrochloric acid. The system was then allowed to cool to 25° C. and concentrated, thereby giving a light yellow solid. The resulting solid was charged into a mixed solvent composed of 250 g of toluene and 250 g of methanol, and suspended at 50° C., and the insolubles were removed by filtration under heating. The resulting filtrate was concentrated and dried under reduced pressure, thereby giving 22.8 g (yield, 79%) of light yellow crystals of free form of N-lauroyl-Gly-His.

$^1$H-NMR (300 MHz, DMSO-d$_6$, δ ppm): 8.12 (s, 1H), 7.78 (d, J=6.6 Hz, 1H), 7.46 (s, 1H), 6.70 (s, 1H), 4.15 (d, J=5.8 Hz, 1H), 3.66-3.60 (m, 2H), 2.90-2.85 (m, 2H), 2.11 (t, J=7.2 Hz, 2H), 1.48-1.23 (m, 18H), 0.84 (t, J=3.7 Hz, 3H)

MS (ESI) m/z: 395.5 (M+H)$^+$.

Example 30

Synthesis of N-Myristoyl-Gly-Methyl

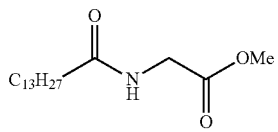

A 500 mL four-neck flask was charged with 14.6 g (115.9 mmol) of glycine methyl ester hydrochloride, 12.3 g (115.9 mmol) of sodium carbon as the base, 110 g of water and 66 g of toluene as the organic solvent, and the flask contents were stirred. Next, a solution of 22 g (89.1 mmol) of myristoyl chloride dissolved in 132 g of toluene was added dropwise thereto over a period of 1 hour at a reaction temperature of 25±5° C. The system was stirred at 25° C. for 2 hours, following which another 100 g of water was added and stirring was continued for 1 hour. Filtration was then carried out, and the filtered matter was collected and dried in vacuo. The filtrate was subjected to liquid separation treatment, and the organic phase was concentrated under reduced pressure and dried in vacuo. The solids obtained from each of these operations were added together, giving 26.8 g (yield, 100%) of white crystals of N-myristoyl-Gly-methyl.

$^1$H-NMR (300 MHz, CDCl$_3$, δ ppm): 5.92 (s, 1H), 4.03 (t, J=7.7 Hz, 2H), 3.77 (s, 3H), 2.24 (t, J=7.6 Hz, 2H), 1.65-1.25 (m, 22H), 0.88 (t, J=6.7 Hz, 3H)

MS (ES) m/z: 300.0 (M+H)$^+$.

Melting point: 72.5° C.

Example 31

Synthesis of Free form of N-Myristoyl-Gly-His

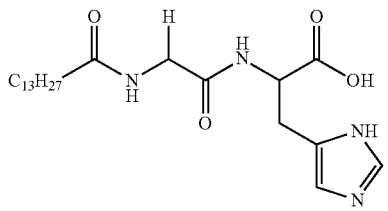

A 500 mL four-neck flask was charged with 10.4 g (66.8 mmol) of L-histidine, 20.0 g (66.8 mmol) of N-myristoyl-Gly-methyl, 200 g of cyclohexane and 8.0 g of methanol, and the flask contents were stirred under heating at 60° C. on an oil bath. Next, 25.8 g (133.6 mmol) of a 28% methanol solution of sodium methoxide as the base was added and stirring was continued for 2 hours at about 60° C. The reaction solution was then concentrated, and subsequently dried in vacuo, thereby giving a clay-like solid. The resulting solid was added to a mixed solution composed of 250 g of toluene and 250 g of methanol, suspended at 50° C., and the insolubles were removed by filtration under heating. The resulting filtrate was added dropwise to 1 L of acetonitrile cooled to −10° C., whereupon a white solid deposited out. The white solid obtained by filtering this solution was dried under reduced pressure, giving 19.5 g (yield, 69%) of light yellow crystals of free form of N-myristoyl-Gly-His.

$^1$H-NMR (300 MHz, DMSO-d$_6$, δ ppm): 8.06 (t, J=7.3 Hz, 2H), 7.56 (s, 1H), 6.80 (s, 1H), 4.35 (d, J=6.9 Hz, 2H), 3.67 (d, J=5.5 Hz, 2H), 2.92 (dd, J1=14.6 Hz, J2=9.1 Hz, 2H), 2.12 (t, J=7.3 Hz, 2H), 1.49-1.02 (m, 22H), 0.85 (t, J=3.7 Hz, 3H)

MS (ESI) m/z: 423.0 (M+H)$^+$.

Example 32

Synthesis of N-Stearoyl-Leu-Methyl

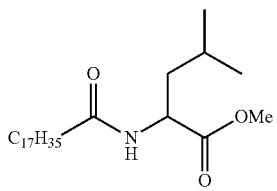

A 500 mL four-neck flask was charged with 15.5 g (85.8 mmol) of L-leucine methyl ester hydrochloride, 9.1 g (85.8 mmol) of sodium carbonate as the base, 100 g of water and 60 g of toluene as the organic solvent, and the flask contents were stirred. Next, a solution of 20 g (66.0 mmol) of stearoyl chloride dissolved in 120 g of toluene was added dropwise thereto over a period of 1 hour at a reaction temperature of 25±5° C. The system was stirred for 2 hours at 25° C., following which another 100 g of water was added and stirring was continued for 1 hour. The organic phase was separated off, concentrated under reduced pressure and dried in vacuo, giving 27.3 g (yield, 100%) of white crystals of N-stearoyl-Leu-methyl.

$^1$H-NMR (300 MHz, CDCl$_3$, δ ppm): 5.77 (d, J=8.3 Hz, 1H), 4.66 (td, J1=8.6 Hz, J2=5.0 Hz, 1H), 3.73 (s, 3H), 2.21 (t, J=7.6 Hz, 2H), 1.69-0.87 (m, 42H)

MS (ESI) m/z: 412.1 (M+H)$^+$.

Melting point: 62.4° C.

Example 33

Synthesis of Free form of N-Stearoyl-Leu-Trp

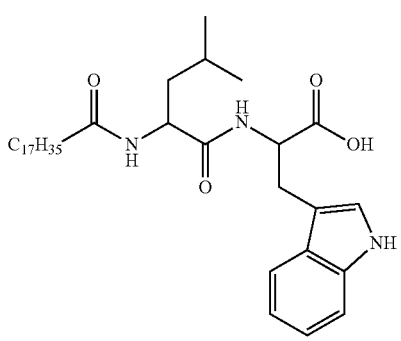

A 100 mL four-neck flask was charged with 1.49 g (7.3 mmol) of L-tryptophan, 3.0 g (7.3 mmol) of N-stearoyl-Leu-methyl, 30 g of cyclohexane and 1.2 g of methanol, and the flask contents were stirred under heating at 60° C. on an oil bath. Next, 2.8 g (14.6 mmol) of a 28% methanol solution of sodium methoxide as the base was added, and stirring was continued for 20 hours at about 60° C. The oil bath was then removed, 0.6 g of methanol was added, and the system was allowed to cool to 25° C. This solution was added under stirring at 35° C. to a mixed solution composed of 50 g of water, 68 g of methanol and 2.4 g (14.6 mmol) of 6N hydrochloric acid. Following addition of the entire amount, the solvent was driven off by drying under reduced pressure, following which ethyl acetate was added to the residue and filtration was carried out under heating at 60° C. The filtrate was dried under reduced pressure, thereby giving 4.0 g (yield, 95%) of free form of N-stearoyl-Leu-Trp.

$^1$H-NMR (300 MHz, MeOD-d$_4$, δ ppm): 7.48 (d, J=6.3 Hz, 1H), 7.19 (dd, J=2.5 Hz, J=0.3 Hz, 1H), 6.99-6.83 (m, 3H), 4.40 (t, J=5.6 Hz, 1H), 4.28 (dd, J=9.1 Hz, J=5.5 Hz, 2H), 3.19 (m, 2H), 2.14 (t, J=4.2 Hz, 1H), 1.97 (t, J=7.2 Hz, 1H), 1.60-1.17 (m, 31H), 0.87-0.69 (m, 9H)

MS (ESI) m/z: 584.1 (M+H)$^+$.

Example 34

Synthesis of Free form of N-Stearoyl-Leu-His

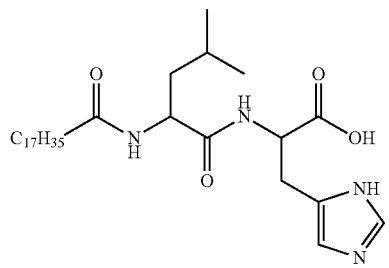

A 100 mL four-neck flask was charged with 1.13 g (7.29 mmol) of L-histidine, 3.00 g (7.29 mmol) of N-stearoyl-Leu-methyl, 30 g of cyclohexane and 2.8 g of methanol, and the flask contents were stirred under heating at 60° C. on an oil bath. Next, 2.9 g (14.6 mmol) of a 28% methanol solution of sodium methoxide as the base was added, and stirring was continued for 3 hours at about 60° C. The oil bath was then removed, 0.6 g of methanol was added, and the solution was allowed to cool to 25° C., following which the solution was added under stirring at 25° C. to a mixed solution composed of 39.1 g of water, 35.8 g of methanol and 2.43 mL (14.6 mmol) of 6N hydrochloric acid. After addition of the entire amount was completed, the reaction solution was heated to 60° C. and stirred for 1 hour. By dropping this solution into ice-cooled acetonitrile, solids were induced to deposit out and were collected by filtration. The resulting solids were dried under reduced pressure, giving 1.2 g (yield, 27%) of white crystals of free form of N-stearoyl-Leu-Trp.

$^1$H-NMR (300 MHz, DMSO-d$_6$, δ ppm): 8.22-8.17 (m, 1H), 8.01-7.90 (m, 2H), 7.05-6.96 (m, 1H), 4.42-4.27 (m, 2H), 3.10-2.92 (m, 4H), 2.11-2.08 (m, 2H), 1.60-1.43 (m, 3H), 1.35-1.05 (m, 28H), 0.86-0.76 (m, 9H)

MS (ESI) ink: 535.1 (M+H)$^+$.

Example 35

Synthesis of N-Stearoyl-Val-Methyl

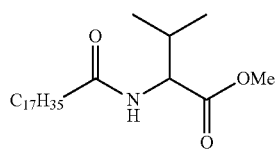

A 500 mL four-neck flask was charged with 10.8 g (64.3 mmol) of L-valine methyl ester, 6.82 g (64.3 mmol) of sodium carbonate as the base, 75 g of water and 45 g of toluene as the organic solvent, following which the flask contents were stirred. Next, a solution of 15.0 g (49.5 mmol) of stearoyl chloride dissolved in 90 g of toluene was added dropwise thereto over a period of 15 minutes at a reaction temperature of 25±5° C. After 17 hours of stirring at 25° C., another 150 g of water was added and additional stirring was carried out, following which the organic phase was separated off. The organic phase was washed twice with 150 g of water, then concentrated under reduced pressure and dried in vacuo, giving 19.7 g (yield, 100%) of white crystals of N-stearoyl-Val-methyl.

$^1$H-NMR (300 MHz, CDCl$_3$, δ ppm): 5.89 (d, J=8.7 Hz, 1H), 4.59 (dd, J=8.7 Hz, 8.7 Hz, 1H), 3.74 (s, 3H), 2.23 (t, J=7.5 Hz, 2H), 2.22-2.18 (m, 1H), 1.72-1.56 (m, 2H), 1.34-1.22 (m, 28H), 0.98-0.82 (m, 9H)

MS (ESI) m/z: 398.3 (M+H)$^+$.

Melting point: 75.7° C. (N=2)

Example 36

Synthesis of Free form of N-Stearoyl-Val-His

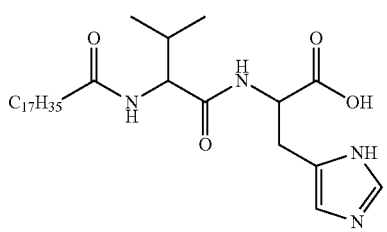

To a 200 mL autoclave was added 1.17 g (7.54 mmol) of L-histidine, 3.00 g (7.54 mmol) of N-stearoyl-Val-methyl, 30 g of cyclohexane, 1.2 g of methanol and 2.91 g (15.1 mmol) of a 28% methanol solution of sodium methoxide as the base, and stirring was continued for 4 hours at about 110° C. The solution was allowed to cool to 25° C. under stirring, after which 10.0 g of water and 30.0 g of methanol were added to the solution, followed by the addition of 2.51 mL (15.1 mmol) of 6N hydrochloride acid. By re-precipitating this solution in 200 g of acetonitrile, a solid was made to deposit out, and the solid was collected by filtration. Next, 100 g of water was added to the resulting solid and stirred for 1 hour, and the resulting solution was re-precipitated in 200 g of acetonitrile, after which the solid that formed was collected by filtration. The resulting solid was dried under reduced pressure, giving 0.41 g (yield, 11%) of light brown crystals of free form of N-stearoyl-Val-His.

$^1$H-NMR (300 MHz, DMSO-d$_6$, δ ppm): 8.15 (d, J=7.8 Hz, 1H), 7.85-7.65 (m, 1H), 7.60-7.50 (m, 1H), 6.85-6.70 (m, 1H), 4.45-4.20 (m, 1H), 4.25-4.10 (m, 2H), 3.00-2.75 (m, 2H), 2.25-1.80 (m, 4H), 1.60-1.35 (m, 2H), 1.35-1.10 (m, 26H), 0.90-0.60 (m, 9H)

MS (ESI) m/z: 521.1 (M+H)$^+$.

Melting point: 196.5° C. (N=2)

Example 37

Synthesis of Free Form of N-Palmitoyl-Gly-His Using Solid NaOMe

A 100 mL four-neck flask was charged with 0.14 g (0.92 mmol) of L-histidine, 0.30 g (0.92 mmol) of N-palmitoyl-Gly-methyl, 3.0 g of toluene, 0.10 g (1.8 mmol) of solid sodium methoxide as the base, and 0.25 g of methanol, following which the flask contents were stirred for 1 hour at about 60° C.

The relative area percentage of the target compound obtained by HPLC (RID detector) analysis, and the N-palmitoyl-Gly-methyl conversion results calculated therefrom are shown below.

TABLE 4

| EX | Methanol added | Conversion[1] | Target compound[2] | Hydrolysate[3] | Starting material[4] |
|---|---|---|---|---|---|
| 32 | 0.25 g | 90% | 67% | 23% | 10% |

[1]Conversion (%) = (Area % of target compound + Area % of hydrolyzate)/(Area % of target compound + Area % of hydrolyzate + Area % of starting compound)
[2]Target compound: free form of N-palmitoyl-Gly-His
[3]Hydrolyzate: N-palmitoyl-Gly
[4]Starting compound: N-palmitoyl-Gly-methyl

Example 38

Comparison of Base Equivalents

A 50 mL four-neck flask was charged with 2 g (6.1 mmol) of N-palmitoyl-Gly-methyl, 0.95 g (6.1 mmol) of L-histidine, 20 g of cyclohexane as the organic solvent and a 28% methanol solution of sodium methoxide as the base, and the temperature was raised to 60° C. under stirring. The reaction was then carried out at 60±5° C. The equivalents of the 28% methanol solution of sodium methoxide with respect to the N-palmitoyl-Gly-methyl, the reaction time, and the amount of free form of N-palmitoyl-Gly-His that formed as determined by HPLC analysis are shown below.

TABLE 5

| Base equivalent (eq.) | Reaction time (h) | Amount of formation (%) of free form of N-palmitoyl-Gly-His |
|---|---|---|
| 1.1 | 4 | 84 |
| 1.3 | 3 | 89 |
| 1.5 | 4 | 93 |
| 1.7 | 2 | 94 |

Therefore, even in cases where 1 to 2 equivalents of base are used, the reaction proceeds well.

The invention claimed is:

1. A method of preparing a lipopeptide compound of formula (3):

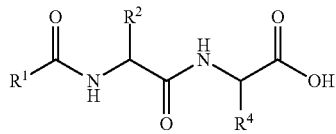

where:
R$^1$ is a C$_{9-23}$ aliphatic group;
R$^2$ is a hydrogen atom or a C$_{1-4}$ alkyl group which may have a C$_{1-2}$ branch; and
R$^4$ is a —(CH$_2$)$_n$-X group in which n is a number from 1 to 4 and X is an amino group, a guanidino group, a —CONH$_2$ group, a 5-membered or 6-membered ring which may contain from 1 to 3 nitrogen atoms, or a fused heterocycle composed of a 5-membered ring and a 6-membered ring; or
a pharmaceutically usable salt thereof, the method comprising:
reacting an ester compound of formula (1):

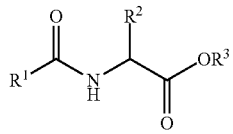

where:
R$^1$ and R$^2$ are as defined above, and
R$^3$ is a C$_{1-6}$ alkyl group, a C$_{1-6}$ haloalkyl group, a C$_{1-6}$ hydroxyalkyl group, or an aryl group which may be substituted with a C$_{1-6}$ alkyl group,
with an α-amino acid compound of formula (2):

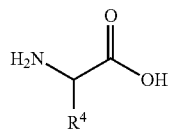

where R$^4$ is as defined above,
in the presence of a base, within a solvent containing a nonpolar organic solvent, and an alcohol, and without use of protecting groups.

2. The preparation method according to claim 1, wherein either n is a number from 1 to 4 and X is an amino group, a guanidino group or a —CONH$_2$ group, or n is 1 and X is a pyrrole group, an imidazole group, a pyrazole group or an imidazole group.

3. The preparation method according to claim 1, wherein R$^1$ is a C$_{11-21}$ linear aliphatic group which may have from 0 to 2 unsaturated bonds.

4. The preparation method according to claim 1, wherein R$^2$ is a hydrogen atom or a C$_{1-3}$ alkyl group which may have a C$_1$ branch.

5. The preparation method according to claim 1, wherein R$^2$ is a hydrogen atom, methyl, ethyl, n-propyl, isopropyl, n-butyl, isobutyl, sec-butyl or tert-butyl group; and R$^4$ is an aminomethyl, aminoethyl, 3-aminopropyl, 4-aminobutyl, carbamoylmethyl, 2-carbamoylethyl, 3-carbamoylbutyl, 2-guanidinoethyl, 3-guanidinopropyl, pyrrolemethyl, imidazolemethyl, pyrazolemethyl or 3-indolemethyl group.

6. The preparation method according to claim 5, wherein R$^2$ is a hydrogen atom, methyl, isopropyl, isobutyl or sec-butyl group; and R$^4$ is a 4-aminobutyl, carbamoylmethyl, 2-carbamoylethyl, 3-guanidinopropyl, imidazolemethyl or 3-indolemethyl group.

7. The preparation method according to claim 1, wherein R$^3$ is a methyl or ethyl group.

8. The preparation method according to claim 1, wherein the base is at least one selected from among alkali metals, inorganic acid salts of alkali metals, alkali metal hydroxides, alkali metal alkoxides, alicyclic amines, and alcohol solutions or alcohol dispersions thereof.

9. The preparation method according to claim 8, wherein the base is at least one selected from among a metallic sodium, metallic potassium, sodium carbonate, potassium carbonate, potassium phosphate, sodium phosphate, sodium hydroxide, potassium hydroxide, sodium methoxide, sodium ethoxide, potassium methoxide, potassium ethoxide, potassium t-butoxide, 1,8-diazabicyclo[5.4.0]-7-undecene, 1,5-diazabicyclo[4.3.0]-5-nonene, and alcohol solutions or alcohol dispersions thereof.

10. The preparation method according to claim 9, wherein the base is selected from among sodium methoxide and methanol solutions or methanol dispersions thereof.

11. The preparation method according to claim 1, wherein the nonpolar organic solvent is at least one selected from the group consisting of aromatic compounds, saturated aliphatic compounds and unsaturated aliphatic compounds.

12. The preparation method according to claim 11, wherein the nonpolar organic solvent is at least one selected from the group consisting of toluene, xylene, ortho-dichlorobenzene, pentane, hexane, heptane, octane, cyclopentane, cyclohexane, methylcyclohexane, cycloheptane and 1-hexene.

13. The preparation method according to claim 1, wherein the solvent includes cyclohexane and methanol or ethanol.

14. The preparation method according to claim 1, wherein the reaction of the ester compound of formula (1) with the α-amino acid compound of formula (2) is carried out at a reaction temperature of 60±5° C.

15. The preparation method according to claim 1, which includes a step of neutralizing with a hydrogen halide a product obtained from the reaction of the ester compound of formula (1) with the α-amino acid compound of formula (2).

16. The preparation method according to claim 15, wherein the neutralization step is carried out in a solvent containing water and an alcohol.

17. A method of preparing a lipopeptide compound of formula (3):

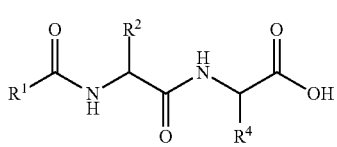

where:
R$^1$ is a C$_{9-23}$ aliphatic group;
R$^2$ is a hydrogen atom or a C$_{1-4}$ alkyl group which may have a C$_{1-2}$ branch; and $R^4$ is a hydrogen atom, a $C_{1-7}$ alkyl group which may have a $C_{1-3}$ branch, a phenylmethyl group, a phenyethyl group, a $—(CH_2)_n$-X group in which n is a number from 1 to 4 and X is an amino group, a guanidino group, a $—CONH_2$ group, a 5-membered or 6-membered ring which may contain from 1 to 3 nitrogen atoms, or a fused heterocycle composed of a 5-membered ring and a 6-membered ring, or a pharmaceutically usable salt thereof, the method comprising:

a step of reacting a compound of formula (4):

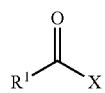
(4)

where X is a halogen atom, a $C_{1-6}$ alkoxy group, or a $—OC(O)R^1$ group in which $R^1$ is as defined above, with a compound of formula (5):

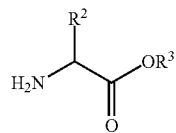
(5)

where:
R² is as defined above, and
R³ is a $C_{1-6}$ alkyl group, a $C_{1-6}$ haloalkyl group, a $C_{1-6}$ hydroxyalkyl group, or an aryl group which may be substituted with a $C_{1-6}$ alkyl group, to obtain an ester compound of formula (1):

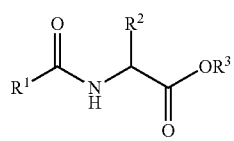
(1)

where: R² and R³ are as defined above; and a step of reacting the ester compound of formula (1) with an α-amino acid compound of formula (2):

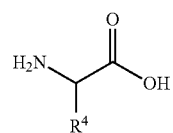
(2)

where R⁴ is as defined above,
in the presence of a base and within a solvent containing a nonpolar organic solvent and an alcohol.

18. The preparation method according to claim 15, wherein the hydrogen halide is at least one selected from the group consisting of hydrochloric acid and hydrobromic acid.

* * * * *